US012595316B2

(12) United States Patent
Hibbert et al.

(10) Patent No.: US 12,595,316 B2
(45) Date of Patent: Apr. 7, 2026

(54) BISPECIFIC AND MULTISPECIFIC ANTIBODIES AND METHOD FOR ISOLATION OF SUCH

(71) Applicant: GENMAB A/S, Valby (DK)

(72) Inventors: Richard G. Hibbert, Utrecht (NL);
Aran F. Labrijn, Nigtevecht (NL);
Arnout F. Gerritsen, Bunnik (NL);
Janine Schuurman, Diemen (NL);
Paul Parren, Odijk (NL)

(73) Assignee: GENMAB A/S, Valby (DK)

( * ) Notice: Subject to any disclaimer, the term of this patent is extended or adjusted under 35 U.S.C. 154(b) by 621 days.

(21) Appl. No.: 15/742,803

(22) PCT Filed: Jul. 1, 2016

(86) PCT No.: PCT/EP2016/065576
§ 371 (c)(1),
(2) Date: Jan. 8, 2018

(87) PCT Pub. No.: WO2017/005649
PCT Pub. Date: Jan. 12, 2017

(65) Prior Publication Data
US 2018/0201693 A1 Jul. 19, 2018

(30) Foreign Application Priority Data

Jul. 9, 2015 (DK) ............................ PA 2015 00399

(51) Int. Cl.
*C07K 16/46* (2006.01)
*C07K 16/28* (2006.01)

(52) U.S. Cl.
CPC ........ *C07K 16/468* (2013.01); *C07K 16/2863* (2013.01); *C07K 16/2887* (2013.01); *C07K 2317/21* (2013.01); *C07K 2317/24* (2013.01); *C07K 2317/31* (2013.01); *C07K 2317/515* (2013.01); *C07K 2317/526* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 8,236,931 B2 * | 8/2012 | De Wildt | A61P 37/02 |
| | | | 530/387.3 |
| 8,586,713 B2 | 11/2013 | Davis et al. | |
| 2010/0331527 A1 | 12/2010 | Davis et al. | |
| 2014/0066599 A2 | 3/2014 | Blein et al. | |
| 2014/0088295 A1 * | 3/2014 | Smith | C07K 16/2887 |
| | | | 530/387.3 |

FOREIGN PATENT DOCUMENTS

| | | | | | |
|---|---|---|---|---|---|
| EP | 1870459 | A1 | 12/2007 | | |
| EP | 2522724 | A1 | 11/2012 | | |
| WO | 02100348 | A2 | 12/2002 | | |
| WO | 2004035607 | A2 | 4/2004 | | |
| WO | 2007/110205 | A2 | 10/2007 | | |
| WO | 2008/052933 | A2 | 5/2008 | | |
| WO | 2008/119353 | A1 | 10/2008 | | |
| WO | 2009/080251 | A1 | 7/2009 | | |
| WO | 2009/089004 | A1 | 7/2009 | | |
| WO | 2010/151792 | A1 | 12/2010 | | |
| WO | 2011/131746 | A2 | 10/2011 | | |
| WO | 2011147986 | A1 | 12/2011 | | |
| WO | 2012143524 | A2 | 10/2012 | | |
| WO | 2013060867 | A2 | 5/2013 | | |
| WO | WO-2013088259 | A2 * | 6/2013 | ........... | C07K 16/249 |
| WO | 2013/136186 | A2 | 9/2013 | | |
| WO | 2014/049003 | A1 | 4/2014 | | |
| WO | WO-2014052717 | A2 * | 4/2014 | .............. | A61J 1/065 |

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
Skolnick et al.(Trends Biotechnol. Jan. 2000;18(1):34-9) (Year: 2000).*
Burgess et al. (J. Cell Biol. 111:2129-2138) (Year: 1990).*
Miosge (Proc Natl Acad Sci U S A. Sep. 15, 2015;112(37):E5189-98) (Year: 2015).*
Bork (Genome Research, 2000, 10:398-400) (Year: 2000).*
UniProt Accession A2P1G9 (downloaded from https://www.uniprot.org/uniprotkb/A2P1G9/entry on Apr. 6, 2024) (Year: 2024).*
UniProt PODOX7 (downloaded from https://www.uniprot.org/uniprotkb/PODOX7/entry on Apr. 6, 2024) (Year: 2024).*
Lindhofer, H. et al., "Preferential species-restricted heavy/light chain pairing in rat/mouse quadromas. Implications for a single-step purification of bispecific antibodies," J Immunol., vol. 155(1):219-225 (1995).
Nilson, B.H.K et al., "Purification of antibodies using protein L-binding framework structures in the light chain variable domain," Journal of Immunological Methods, vol. 164(1):33-40 (1993).
Experimental work: Declaration from WuXi Biologics, 9 pages, Oct. 1, 2024.
Fisher, N. et al., "Exploiting light chains for the scalable generation and platform purification of native human bispecific IgG," Nat Commun., vol. 6 (6113): 12 pages (2014).

(Continued)

*Primary Examiner* — Brian Gangle

*Assistant Examiner* — Andrea K McCollum

(74) *Attorney, Agent, or Firm* — Nelson Mullins Riley & Scarborough LLP; Jane E. Remillard, Esq.; Christopher L. Frank

(57) ABSTRACT

Novel bispecific and multispecific antibodies having differentially modified light chains, that allows for isolation of the bispecific or multispecific antibodies based on a differential affinity towards an affinity reagent.

22 Claims, 15 Drawing Sheets
Specification includes a Sequence Listing.

(56) References Cited

OTHER PUBLICATIONS

Graille, M. et al., "Complex between Peptostreptococcus magnus Protein L and a Human Antibody Reveals Structural Convergence in the Interaction Modes of Fab Binding Proteins," Structure, vol. 9: 679-687 (2001).

Gramer, M. et al., "Production of stable bispecific IgG1 by controlled Fab-arm exchange: scalability from bench to large-scale manufacturing by application of standard approaches," MAbs, vol. 5(6):962-973 (2013).

Housden, N.G. et al., "Immunoglobulin-binding domains: Protein L from Peptostreptococcus magnus," Biochem Soc Trans., vol. 31(Pt 3):716-718 (2003).

James, L. et al., "Beta-Edge Interactions in a Pentadecameric Human Antibody Vic, Domain," J. Mol. Biol., vol. 367:603-608 (2007).

Labrijn, A. et al.,"Controlled Fab-arm exchange for the generation of stable bispecific IgG1," Nat Protoc., vol. 9 (10):2450-2463 (2014).

Muzard, J. et al., "Grafting of protein L-binding activity onto recombinant antibody fragments, "Analytical Biochemistry, vol. 388:331-338 (2009).

Rispens, T. et al., "Mechanism of immunoglobulin G4 Fab-arm exchange," J Am Chem Soc., vol. 133 (26):10302-10311 (2011).

Marvin and Zhu, "Recombinant approaches to IgG-like bispecific antibodies," Acta Pharmacologica Sinica, vol. 26(6):649-658 (2005).

Roque, A. et al., "Affinity-based methodologies and ligands for antibody purification: advances and perspectives," Journal of Chromatography A, vol. 1160:44-45 (2007).

Handbook of Therapeutic Antibodies, Second Edition, Chapter 11 Bispecific Antibodies, pp. 267-310 (2014).

Experimental work: Summary of products and sequences for Declaration from WuXi Biologics, 2 pages, Oct. 1, 2024.

Further Written Submissions, filed in EP Patent No. 3319996, 10 pages, Oct. 20, 2025.

Notice of Opposition, filed in EP Patent No. 3319996, 30 pages, Oct. 9, 2024.

Response to Notice Notices of Opposition, filed in EP Patent No. 3319996, 58 pages, Feb. 17, 2025.

Response to Patentee's Notice of Opposition, filed in EP Patent No. 3319996, 28 pages, Jun. 13, 2025.

Response to Proprietor's Submission, filed in EP Patent No. 3319996, 29 pages, May 14, 2025.

Second Notice of Opposition, filed in EP Patent No. 3319996, 46 pages, Oct. 9, 2024.

Graille, M, et al., "Evidence for Plasticity and Structural Mimicry at the Immunoglobulin Light Chain-Protein L Interface*," American Society for Biochemistry and Molecular Biology, 277(49), :47500-47506 (2002).

Kabat, E. et al., "Sequences of proteins of immunological interest," US Department of Health and Human Services 5th Edition, 15 pages (1991).

Krissinel et al., "Inference of Macromolecular Assemblies from Crystalline State," J. Mol. Biol., vol. 372: 774-797 (2007).

Labrijn, A et al., "Species-specific determinants in the IgG CH3 domain enable Fab-arm exchange by affecting the Noncovalent CH3-CH3 Interaction Strenght, "J. Immunol., vol. 187(6): 3238-3246 (2011).

Labrijn, A.F., et al., "Efficient generation of stable bispecific IgG1 by controlled Fab-arm exchange," PNAS, vol. 110(13): 5145-5150 (2013).

Laemmli U. K., "Cleavage of Structural Proteins during the Assembly of the Head of Bacteriophage T4," Nature Publishing Group , vol. 227: 680-685 (1970).

Lefranc, M-P. et al., "IIMGT, the international ImMunoGeneTics information system 25 years on" Dev Comp Immunol, vol. 27: 55-77 (2003).

Nilson, B. et al., "Protein L from Peptostreptococcus magnus binds to the kappa light chain variable domain," 8 American Society for Biochemistry and Molecular Biology, vol. 267(4): 2234-2239 (1992).

* cited by examiner

```
                                    1         1         1         1         1         1
                                    1         2         3         4         5         6
CROSS-REACTIVE                      901234567890123456789012345678901234567890123456 78 901
UP|P01834|IGKC1_Homsap              TVAAPSVFIFPPSDEQLKSGTASVVCLLNNFYPREAKVQWKVDNALQSGN SQE
IMGT|M11736|IGKC2_Homsap            TVAAPSVFIFPPSDEQLKSGTASVVCLLNNFYPREAKVQWKVDNALQSGN SQE
IMGT|M11737|IGKC3_Homsap            TVAAPSVFIFPPSDEQLKSGTASVVCLLNNFYPREAKVQRKVDNALQSGN SQE
GB|AF017732|IGKC4_Homsap            TVAAPSVFIFPPSDEQLKSGTASVVCLLNNFYPREAKVQWKVDNVLQSGN SQE
GB|AF113887|IGKC5_Homsap            TVAAPSVFIFPPSDEQLKSGTASVVCLLNNFYPREAKVQWKVDNALQSGN SQE
GB|AJ619771|IGKC_Macfas             AVAAPSVFIFPPSEDQVKSGTVSVVCLLNNFYPREASVKWKVDGAVQTGN SQE
GB|FJ795855|IGKC_Macmul             AVAAPSVLIFPPSEDQVKSGTVSVVCLLNNFYPREASVKWKVDGVLKTGN SQE
CONCENSUS +                          VAAPSV IFPPS  Q KSGT SVVCLLNNFYPREA V  KVD      GN SQE NON CROSS-REACTIVE
UP|P01837|IGKC_Musmus               ADAAPTVSIFPPSSEQLTSGGASVVCFLNNFYPKDINVKWKIDGSERQNG VLN
UP|P01844|IGLC2_Musmus              PKSTPTLTVFPPSSEELKENKATLVCLISNFSPSGVTVAWKANGTPITQG VDT
UP|P01845|IGLC3_Musmus              PKSTPTLTMFPPSPEELQENKATLVCLISNFSPSGVTVAWKANGTPITQG VDT
UP|P0CG04|IGLC1_Homsap              PKANPTVTLFPPSSEELQANKATLVCLISDFYPGAVTVAWKADGSPVKAG VET
UP|P0CG05|IGLC2_Homsap              PKAAPSVTLFPPSSEELQANKATLVCLISDFYPGAVTVAWKADSSPVKAG VET
UP|P0CG06|IGLC3_Homsap              PKAAPSVTLFPPSSEELQANKATLVCLISDFYPGAVTVAWKADSSPAKAG VET
UP|P0CF74|IGLC6_Homsap              PKAAPSVTLFPPSSEELQANKATLVCLISDFYPGAVKVAWKADGSPVNTG VET
UP|A0M8Q6|IGLC7_Homsap              PKAAPSVTLFPPSSEELQANKATLVCLVSDFYPGAVTVAWKADGSPVKVG VET
IMGT|V01241|IGKC_Ratnor             ADAAPTVSIFPPSTEQLATGGASVVCLMNNFYPRDISVKWKIDGTERRDG VLD
IMGT|K01360|IGKC1_Orycun            DPVAPTVLIFPPAADQVATGTVTIVCVANKYFPDVT VTWEVDGTTQTTG IEN
IMGT|X00232|IGKC2_Orycun            DPVAPSVLLFPPSKEELTTGTATIVCVANKFYPSDITVTWKVDGTTQQSG IEN
GB|AEM45014|IGKC_Bostau             SDAEPSVFLFKPSDEQLKTGTVSVVCLVNDFYPKDINVKWKVDGVTQSSSNFQN
CONCENSUS -                          V                               EA           GN S E
PISA(INTERFACE)                         + ++ + ++       + +++++ +                     +
SELECTED                             *                             **            ** *    *

1         1         1         2         2
                                   7         8         9         0         1
CROSS-REACTIVE                     23456789012345678901234567890123456789012345678901234
UP|P01834|IGKC1_Homsap             SVTEQDSKDSTYSLSSTLTLSKADYEKHKVYACEVTHQGLSSPVTKSFNRGEC
IMGT|M11736|IGKC2_Homsap           SVTEQESKDSTYSLSSTLTLSKADYEKHKVYAGEVTHQGLSSPVTKSFNRGEC
IMGT|M11737|IGKC3_Homsap           SVTEQESKDSTYSLSSTLTLSKADYEKHKVYACEVTHQGLSSPVTKSFNRGEC
GB|AF017732|IGKC4_Homsap           SVTEQDSKDSTYSLSSTLTLSKADYEKHKLYACEVTHQGLSSPVTKSFNRGEC
GB|AF113887|IGKC5_Homsap           SVTEQDSKDSTYSLSNTLTLSKADYEKHKVYACEVTHQGLSSPVTKSFNRGEC
GB|AJ619771|IGKC_Macfas            SVTEQDSKDNTYSLSSTLTLSSTDYQSHNVYACEVTHQGLSSPVTKSFNRGEC
GB|FJ795855|IGKC_Macmul            SVTEQDSKDNTYSLSSTLTLSSTDYQSHNVYACEVTHQGLSSPVTKSFNRGEC
CONCENSUS +                        SVTE SKD TYSLS TLTLS DY H  YA EVTHQGLSSPVTKSFNRGEC NON CROSS-REACTIVE
UP|P01837|IGKC_Musmus              SWTDQDSKDSTYSMSSTLTLTKDEYERHNSYTCEATHKTSTSPIVKSFNRNEC
UP|P01844|IGLC2_Musmus             SNPTKEGN  KFMASSFLHLTSDQWRSHNSFTCQVTHEGDT   VEKSLSPAECL
UP|P01845|IGLC3_Musmus             SNPTKEDN  KYMASSFLHLTSDQWRSHNSFTCQVTHEGDT   VEKSLSPAECL
UP|P0CG04|IGLC1_Homsap             TKPSKQSN  NKYAASSYLSLTPEQWKSHRSYSCQVTHEGST   VEKTVAPTECS
UP|P0CG05|IGLC2_Homsap             TTPSKQSN  NKYAASSYLSLTPEQWKSHRSYSCQVTHEGST   VEKTVAPTECS
UP|P0CG06|IGLC3_Homsap             TTPSKQSN  NKYAASSYLSLTPEQWKSHKSYSCQVTHEGST   VEKTVAPTECS
UP|P0CF74|IGLC6_Homsap             TTPSKQSN  NKYAASSYLSLTPEQWKSHRSYSCQVTHEGST   VEKTVAPAECS
UP|A0M8Q6|IGLC7_Homsap             TKPSKQSN  NKYAASSYLSLTPEQWKSHRSYSCRVTHEGST   VEKTVAPAECS
IMGT|V01241|IGKC_Ratnor            SVTDQDSKDSTYSMSSTLSLTKADYESHNLYTCEVVHKTSSSPVVKSFNRNEC
IMGT|K01360|IGKC1_Orycun           SKTPQNSADCTYNLSSTLTLTSTQYNSHKEYTCKVT QGTTS VVQSFNRGDC
IMGT|X00232|IGKC2_Orycun           SKTPQSPEDNTYSLSSTLSLTSAQYNSHSVYTCEVV QGSASPIVQSFNRGDC
GB|AEM45014|IGKC_Bostau            SFTDQDSKKSTYSLSSILTLPSSEYQSHNAYTCEVSHKSLTTALVKSFSKNEC
CONCENSUS -                              E                S          A          T          +
PISA(INTERFACE)                    + +         +++       *
SELECTED                               *                 *
```

```
                          1         2         3         4         5         6
                 1234567890123456789012345678901234567890123456789012345678901234
PDB|1MHH_A       DIVMSQSPSSLAVSAGEKVTMSCKSSQSLLNSRTRKNYLAWYQQKPGQSPKVLIYWA-------
PDB|1HEZ_A       DIQMTQSPSSLSASVGDRVTITCRTSQSI------SSYLNWYQQKPGKAPKLLIYAA-------
2F8_VL           AIQLTQSPSSLSASVGDRVTITCRASQDI------SSALVWYQQKPGKAPKLLIYDA-------
SP|P01617|KV204  DIVMTQSPLSLPVTPGEPASISCRSSQSLLHS-DGFDYLNWYLQKPGQSPZLLIYAL-------
SP|P01699|LV101  QSVLTQPP SASGTPGQRVTISCSGGNFDI----GRNSVNWYQVHPGTAPRLLIYSS-------
PISA(INTERFACE)  +++++++ +   ++++++  +
SELECTED         *       *   * * * *  +  *
```

```
                            1         1         1
                  789012345678901234567890123456789012345 67
                    5678901234567890123456789012345678901234567
PDB|1MHH_A        STRESGVP-DRFTGRG--SGTDFTLTISSVQAEDQAVYYCKQAYI----PPLTFGAGTKLELK
PDB|1HEZ_A        SSLQSGVP-SRFSGSG--SGTDFTLTISSLQPEDFATYYCQQSYS----TPRTFGQGTKVEIK
2F8_VL            SSLESGVP-SRFSGSE--SGTDFTLTISSLQPEDFATYYCQQFNS----YPLTFGGGTKVEIK
SP|P01617|KV204   SNRASGVP-DRFSGSG--SGTDFTLKISRVEAEDVGVYYCMZALQ-----APITFGQGTRLEIK
SP|P01699|LV101   DQRSSGVP-DRFSGSK--SGTSASLAISGLQSENEADYFCATWDDS--LDGPVFGGGTKVTVL
PISA(INTERFACE)                                 +
SELECTED                                                             +
                                                                      *
```

IgG1-7D8-K409R

IgG1-7D8-K409R-V110R

IgG1-7D8-K409R-V110K

IgG1-7D8-K409R-V110D

IgG1-7D8-K409R-V110E

IgG1-7D8-K409R-V110T

FIG. 7B                                    FIG. 7C

—— bsIgG1-2F8-V110D/7D8 (load)          —— bsIgG1-2F8-V110D/7D8 (pH 3.5 elution)
---- IgG1-2F8-F405L-V110D                ---- IgG1-2F8-F405L-V110D
······ IgG1-7D8-K409R                    ······ IgG1-7D8-K409R Flow-through    Eluate — bsIgG1-2F8-S12P/1014-169 (load)
---- IgG1-2F8-F405L-S12P
· IgG1-1014-169-K409R — bsIgG1-2F8-S12P/1014-169 (elution)
---- IgG1-2F8-F405L-S12P
IgG1-1014-169-K409R

BISPECIFIC AND MULTISPECIFIC ANTIBODIES AND METHOD FOR ISOLATION OF SUCH

CROSS-REFERENCE TO RELATED APPLICATIONS

This application is a 35 U.S.C. 371 national stage filing of International Application No. PCT/EP2016/065576, filed Jul. 1, 2016, which claims priority to Danish Patent Application No. PA 2015 00399, filed Jul. 9, 2015. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 14, 2020, is named GMI_167US_Sequence_Listing.txt and is 30,325 bytes in size.

FIELD OF THE INVENTION

The present invention relates to novel bispecific and multispecific antibodies, and novel methods for producing and isolating such.

BACKGROUND OF THE INVENTION

Monoclonal antibodies have in recent years become successful therapeutic molecules, in particular for the treatment of cancer. Unfortunately, however, in certain cases monoclonal antibodies are unable to cure diseases when used as monotherapy. Bispecific antibodies can potentially overcome some of the limitations of monoclonal antibody therapy, e.g. they could be used as mediators to target a drug or toxic compound to target cells, as mediators to retarget effector mechanisms to disease-associated sites or as mediators to increase specificity for tumor cells, for example by binding to a combination of targets molecules that is exclusively found on tumor cells.

Many different formats and uses of bispecific and multispecific antibodies have been developed. One of the major obstacles in the development of bispecific antibodies has been the difficulty of producing the material in sufficient quality and quantity by traditional technologies, such as the hybrid hybridoma and chemical conjugation methods. Co-expression of two antibodies, consisting of different heavy and light chains, in a host cell leads to a mixture of possible antibody products in addition to the desired bispecific antibody.

Several strategies have been described to favor the formation of a heterodimeric, i.e. bispecific, product upon co-expression of different antibody constructs in one cell. Lindhofer et al. (1995 J Immunol 155:219) have described that fusion of rat and mouse hydridomas producing different antibodies leads to enrichment of functional bispecific antibodies, because of preferential species-restricted heavy/light chain pairing. Another strategy to promote formation of heterodimers over homodimers upon co-expression of different antibody constructs is by engineering of the CH3-CH3 interface. Examples of such strategies include the "knob-into-hole" strategy (U.S. Pat. No. 5,731,168), electrostatic steering (EP1870459 and WO 2009089004) and the 'strand exchanged engineered domain' (SEED) strategy (WO2007110205).

Alternative to co-expression of different antibodies in one cell to yield bispecific antibodies, the applicant has previously disclosed a post-production method for generating bispecific antibodies in vitro by so called Fab-arm exchange upon separate expression of the monospecific antibodies (WO 2008119353 and WO2011131746). The applicant found that by introducing asymmetrical mutations in the CH3 regions of the two monospecific starting proteins, the Fab-arm exchange reaction can be forced to become directional and yield highly stable heterodimeric proteins.

The methods used for generating a heterodimeric, bispecific product, including the methods described above, can sometimes result in production of a small amount of undesired homodimers. For some applications monovalency is preferred, or required, and in these instances residual, bivalent homodimers may dampen treatment efficacy and/or induce safety concerns. This necessitates further purification of the desired product.

Several methods for purification of (bispecific) antibodies have been described. The bispecific rat/mouse hybrid antibody described by Lindhofer et al (1995 J Immunol 155: 219) can be selectively purified with Protein A, by making use of the intrinsic difference in binding properties of the used mouse and rat antibodies to Protein A: rat IgG2b does not bind Protein A, whereas mouse IgG2a does.

Another approach for isolating bispecific antibodies based on differential Protein A binding has been described in U.S. Pat. No. 8,586,713. In this method the Fc-region of one of the heavy chains is engineered to have reduced affinity for Protein A, allowing isolation of the bispecific antibody by differential binding of the IgG regions to Protein A. Mutations in the Fc-regions, however, may affect Fc-mediated effector functions, such as ADCC and CDC, or the in vivo half-life of antibodies.

Furthermore, various resins have been described that specifically bind to Kappa light chains, such as HiTrap™ Protein L (GE Healthcare®), Capto L™ (GE Healthcare), KappaSelect™ (GE Healthcare), and CaptureSelect KappaXL™ (ThermoFisher®).

A method has been described in which bispecific monoclonal antibodies composed of a single heavy chain and two different light chains (LC), one containing Kappa constant domain and the other a Lambda constant domain, were purified using light chain specific resins (WO2013/088259 A2, Novimmune®). This method is restricted to bispecific antibodies that contain different LC species and specific LC-HC pairing. A method has also been described to purify bispecific antibodies based upon mutations of the CH1 domain (WO2013/136186 A2 Novimmune).

There is still a need for methods to purify heterodimeric binding proteins such as bispecific and multispecific antibodies. It is an object of the present invention to provide methods of purifying heterodimeric binding proteins such as bispecific and multispecific antibodies that contain two or more Kappa light chains using resins that bind to Kappa light chains, combined with mutations that prevent or reduce binding of one or more of the kappa light chains to the resins. It is another object to provide methods to separate bispecific antibodies from the homodimers from which the heterodimeric bispecific antibodies are formed.

SUMMARY OF THE INVENTION

In one aspect the invention relates to a bispecific or multispecific antibody wherein two light chains differ by at least one amino acid which difference results in an improved ability to quickly and effectively isolate the bispecific heterodimeric protein from homodimers, since the difference results in a differential ability of the light chains to bind to an affinity reagent designed specifically to bind to light chains, such as the affinity reagents Protein L, CaptureSelect KappaXL and KappaSelect.

Accordingly, in one aspect the invention relates to a bispecific antibody comprising a first light chain/heavy chain pair comprising a first VL and a first VH region having a first binding specificity and comprising a first light chain constant region and a first heavy chain constant region; and a second light chain/heavy chain pair comprising a second VL and a second VH region having a second binding specificity and comprising a second light chain constant region and a second heavy chain constant region wherein the first light chain comprises a modification that reduces or eliminates binding of the first light chain to an affinity reagent.

In another aspect the invention relates to a method for producing a bispecific antibody product comprising:

a. providing a first antibody having a first binding specificity, said first antibody comprising two light chain/heavy chain pairs, wherein each light chain comprising a modification that reduces or eliminates binding of the light chain to an affinity reagent selected from the group consisting of Protein L, CaptureSelect KappaXL and KappaSelect;

b. providing a second antibody having a second binding specificity, said second antibody comprising two light chain/heavy chain pairs, wherein each light chain is unmodified with respect to binding to the affinity reagent selected in a);

c. generation of a bispecific antibody which bispecific antibody comprises:

a first light chain/heavy chain pair of said first antibody having a first binding specificity and having reduced or eliminated binding of the light chain to an affinity reagent selected from the group consisting of Protein L, CaptureSelect KappaXL and KappaSelect;

and comprising a second light chain/heavy chain pair of said second antibody having a second binding specificity and being unmodified with respect to binding to the affinity reagent selected in a);

d. isolating the bispecific antibody based on the ability of the bispecific antibody to bind to the affinity reagent selected in a).

In a further aspect, the invention relates to a method for isolating a bispecific antibody, comprising isolating from a mixture of antibodies a bispecific antibody having differentially modified light chains, wherein the modification results in a bispecific antibody with heterodimeric light chains whose monomers have a differential affinity for an affinity reagent designed for binding to the light chain constant region of an immunoglobulin and the bispecific antibody is isolated from the mixture based on its affinity for the reagent.

BRIEF DESCRIPTION OF THE FIGURES

FIG. 1: Sequence alignment of kappa light chain CL domains. (allo) indicates allotypic variations; CONSENSUS + indicates conserved residues present in all cross-reactive species; CONSENSUS − indicates "CONSENSUS+" residues that are present in one of the non-cross-reactive species (and human lambda CL); PISA (INTERFACE) indicates residues (+) that are located at the CL-VL and CL-CH1 interfaces with <50% exposed surface area in the PDB 1HZH structure as determined by the PDBePISA tool (pd-be.org/pisa/) (Krissinel, E. and Henrick, K.; J Mol Biol (372):774-97, 2007); Selected residues (*) were mutated to the mouse equivalent. EU-numbering convention is used to annotate amino acid residues (Kabat et al., Sequences of Proteins of Immunological Interest, 5th Ed. Public Health Service, National Institutes of Health, Bethesda, MD. (1991)). (SEQ ID NO: 1—UP|P01834|IGKC1_Homsap, SEQ ID NO: 2—IMGT|M11736|IGKC2_Homsap, SEQ ID NO: 3—IMGT|M11737|IGKC3_Homsap, SEQ ID NO: 4—GB|AF017732|IGKC4_Homsap, SEQ ID NO: 5—GB|AF113887|IGKC5_Homsap, SEQ ID NO: 6—GB|AJ619771|IGKC_Macfas, SEQ ID NO: 7—GB|FJ795855|IGKC_Macmul, SEQ ID NO: 8—UP|P01837|IGKC_Musmus, SEQ ID NO: 9—UP|P01844|IGLC2_Musmus, SEQ ID NO: 10—UP|P01845|IGLC3_Musmus, SEQ ID NO: 11—UP|P0CG04|IGLC1_Homsap, SEQ ID NO: 12—UP|P0CG05|IGLC2_Homsap, SEQ ID NO: 13—UP|P0CG06|IGLC3_Homsap, SEQ ID NO: 14—UP|P0CF74|IGLC6_Homsap, SEQ ID NO: 15—UP|A0M8Q6|IGLC7_Homsap, SEQ ID NO: 16—IMGT|V01241|IGKC_Ratnor, SEQ ID NO: 17—IMGT|K01360|IGKC1_Orycun, SEQ ID NO: 18—IMGT|X00232|IGKC2_Orycun, SEQ ID NO: 19—GB|AEM45014|IGKC_Bostau, and SEQ ID NO: 20—Consensus.)

FIG. 2: Sequence alignment of kappa light chain VL domains. PBD structures 1HEZ and 1MHH were analyzed using the PDBePISA tool (pdbe.org/pisa/) (Krissinel, E. and Henrick, K.; J Mol Biol (372):774-97, 2007). Residues identified as being at the interface with Protein L in all models are marked (+). Selected residues (marked *) were mutated to the equivalent residue found in the kappa subtype V-II (P01617) or Lambda subtype V-1 (P01699) sequences. IMGT numbering is used to annotate amino acid residues (Lefranc, M.-P. et al., Dev. Comp. Immunol., 2003, 27, 55-77). (SEQ ID NO: 21—1 mhh_A, SEQ ID NO: 22—1hez_A, SEQ ID NO: 23—2F8_lc, SEQ ID NO: 24—sp|P01617|KV204, and SEQ ID NO: 25—sp|P01699|LV101.)

(FIG. 3F) Analysis of flow-through fractions from KappaSelect purifications of modified IgG1-2F8 variants using SDS-PAGE. Non-reducing SDS-PAGE gels shows a band of intact IgG1 variants in the flow-through of IgG1-2F8-F405L-mmF135L (lane 1) and IgG1-2F8-F405L-V110D (lane 2) but not the other IgG1-2F8-F405L variants (lanes 3-10). The other major bands are assigned as antibody fragments.

4F) IgG1-7D8-K409R-V110T. The absorption at 280 nm (solid line) and pH (dashed grey line) were monitored. All purifications show an elevated absorption during column loading from non-bound material from the cell culture supernatants in the flow-through. Specifically bound IgG1-7D8-K409R variants were eluted at pH 3.5 and detected by peaks in the absorption at 280 nm. Peaks at 280 nm during the pH 5.0 wash are indicative of less tightly bound material, whereas peaks at 280 nm during the guanidine-HCl wash at approximately 30 mL are caused by an incomplete elution of antibodies during the wash and elution phases.

Figures 5A, 5B:
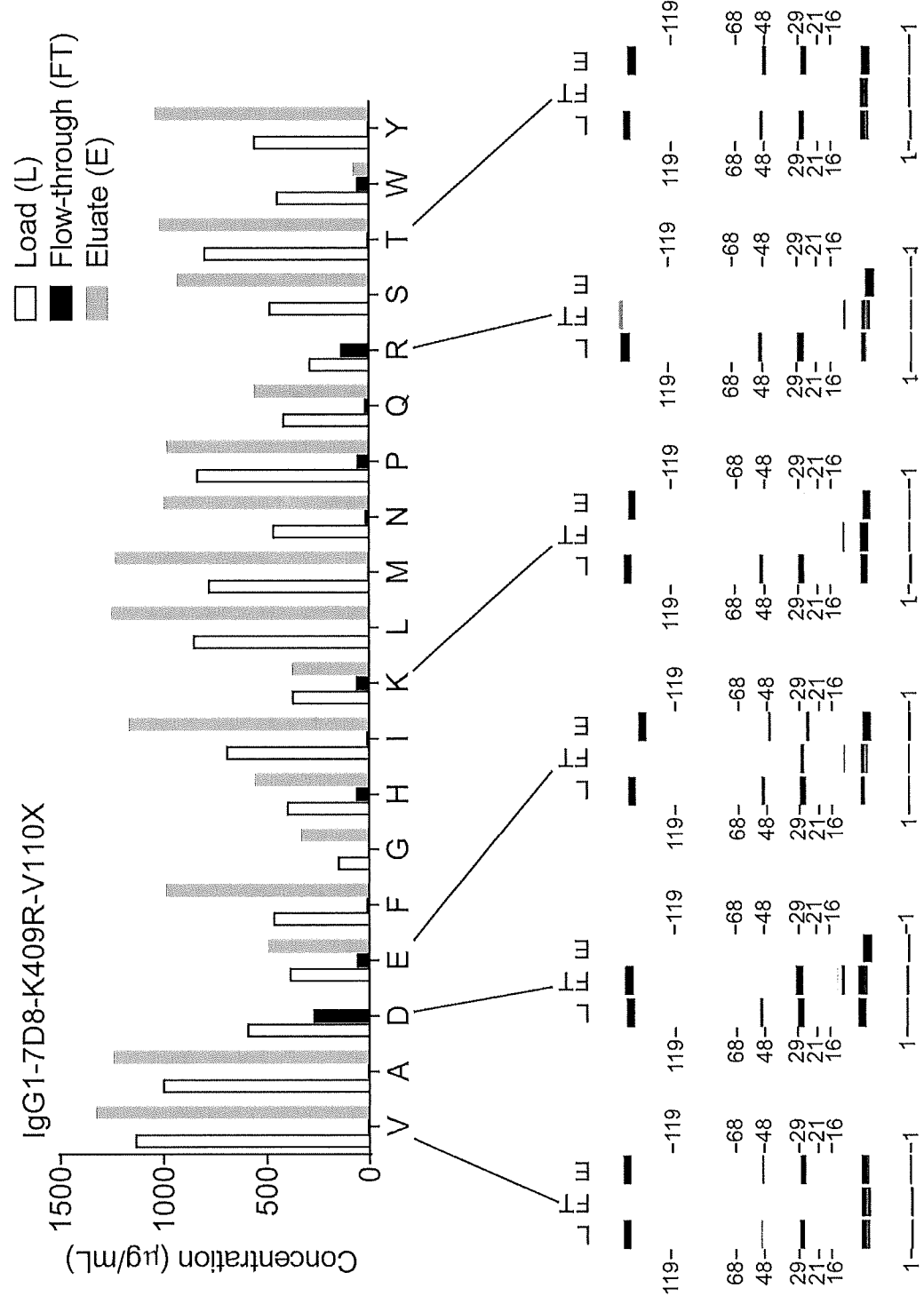

FIGS. 5A and 5B: Analysis of fractions from CaptureSelect KappaXL separations of modified IgG1-7D8-K409R variants using Bio-Layer Interferometry and CE-SDS. (FIG. 5A) The concentration of IgG1-7D8-K409R variants in load samples, pooled flow-through samples and pooled eluate samples were inferred from bio-layer interferometry measurements. The data from the 20 IgG1-7D8-K409R variants, with a different amino acid at position 110 (EU-numbering convention) of the kappa light chain, are grouped and labeled using the single amino acid code for the amino acid at this position. The measured protein concentrations in the flow-through are lower than in the load samples for variants that show no detectable binding to the resin as a result of the dilution of the flow-through samples during the purification experiments. (FIG. 5B) Analysis of fractions from CaptureSelect KappaXL separations of modified IgG1-7D8-K409R variants using CE-SDS. Exemplary non-reducing CE-SDS electropherograms that have been calibrated according to a molecular weight standard, show a band of intact IgG1 variants at a molecular weight of approximately 150 kDa in the load samples of IgG1-7D8-K409R, IgG1-7D8-K409R-V110D, IgG1-7D8-K409R-V110E, IgG1-7D8-K409R-V110K, IgG1-7D8-K409R-V110R and IgG1-7D8-K409R-V110T. Intact IgG1 variants may be detected in flow-through and/or the eluate depending on the relative binding of the IgG1-7D8-K409R variants to the CaptureSelect KappaXL resin. The other major bands of lower molecular weights are assigned as antibody fragments, system calibration peaks or other material from the transient production experiments.

Figure 6A:
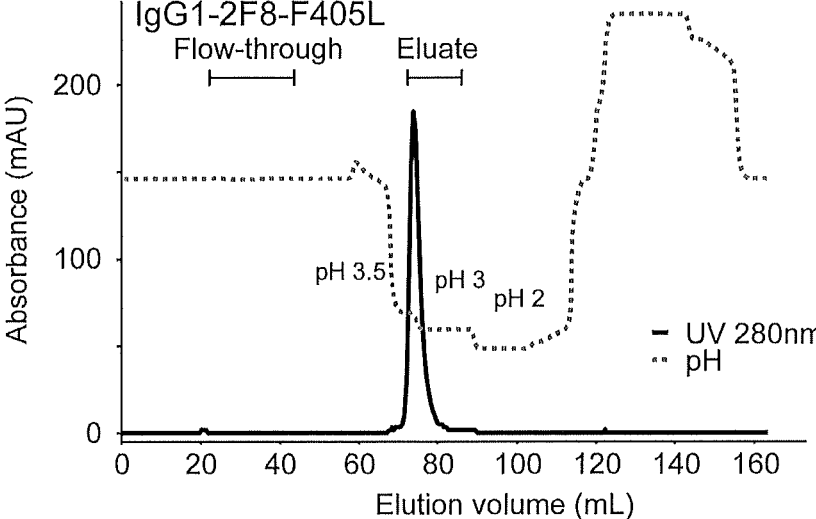
Figure 6B:
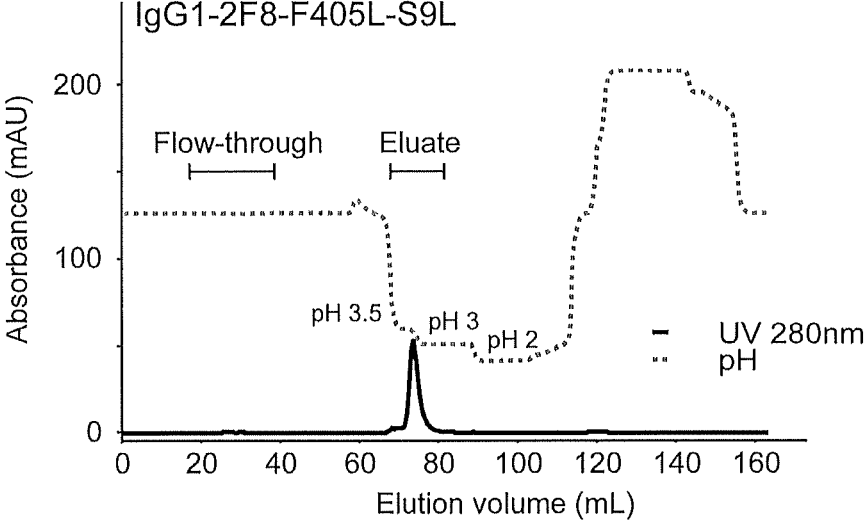
Figure 6C:
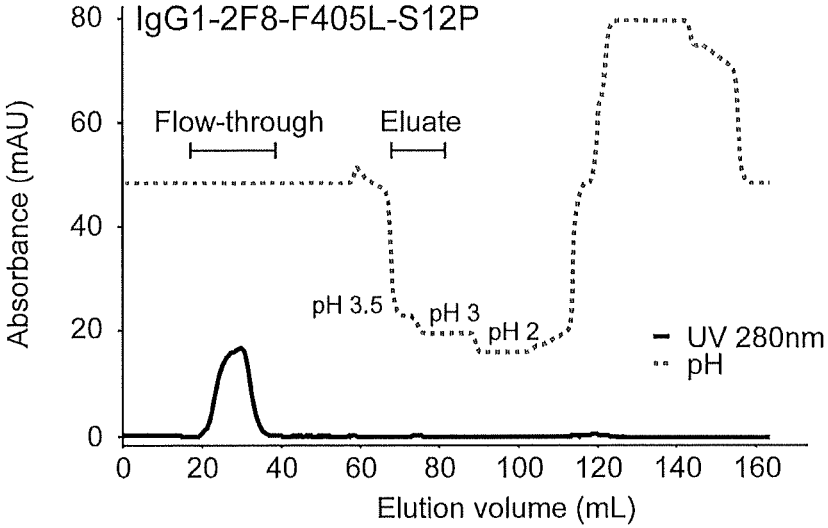

FIGS. 6A-6C: HiTrap Protein L purifications of purified IgG-2F8-F405L variants. Chromatograms showing the absorption at 280 nm (solid line) and the pH profile (dashed grey line) during the separations of purified (FIG. 6A) IgG1-2F8-F405L, (FIG. 6B) IgG1-2F8-F405L-S9L and (FIG. 6C) IgG1-2F8-F405L-S12P.

FIGS. 7A-7E: (FIG. 7A) Exemplary CaptureSelect KappaXL separation of the product of the asymmetric controlled fab arm exchange of IgG1-2F8-F405L-V110D×IgG1-7D8-K409R. Chromatograms show the absorption at 280 nm (solid line) and the pH profile (dashed grey line) during the purification. (FIG. 7B) Quantitation of Bispecific Antibody content using Analytical Hydrophobic Interaction Chromatography. Overlay of HIC profiles of IgG1-2F8-F405L-V110D and IgG1-7D8-K409R parental antibodies (gray dotted and gray dashed lines, respectively) and the pooled chromatography solutions (black solid line) of load sample and (FIG. 7C) eluted sample following CaptureSelect KappaXL purification. (FIG. 7D) Exemplary quantitation of antibody monomer content using HP-SEC. The chromatogram shows the detected signal at 280 nm. The assigned peaks are indicated with triangles. (FIG. 7E) Examplary CE-SDS electropherograms of load sample and eluted end product (EP) sample following CaptureSelect KappaXL purification.

FIGS. 8A-8E: (FIG. 8A) Exemplary HiTrap Protein L separation of the product of the asymmetric controlled Fab-arm exchange of IgG1-2F8-F405L-S12P×IgG1-1014-169-K409R. Chromatograms show the absorption at 280 nm (solid line) and the pH profile (dashed grey line) during the purification. Exemplary Cation Exchange Chromatography (CIEX) characterization of load and end product samples from bispecific antibody purifications. Overlay of CIEX profiles of IgG1-2F8-F405L-S12P and IgG1-1014-169-K409R parental antibodies (gray dotted and gray dashed lines, respectively) and the load material or the (FIG. 8C) end product (black solid line). (FIG. 8D) Exemplary quantitation of antibody monomer content using HP-SEC. The chromatogram shows the detected signal at 280 nm. The assigned peaks are indicated with triangles. (FIG. 8E) Exemplary CE-SDS electropherograms of load sample and eluted end product (EP) sample following Protein L purification.

FIGS. 9A-9D: Binding to CD20-expressing cells or recombinant EGFR by parental and bispecific antibodies containing the V110D or S12P mutations. Concentration series of the indicated bivalent monospecific parental antibodies (FIG. 9A, FIG. 9C) or monovalent bispecific antibodies (FIG. 9B, FIG. 9D) were used to test their ability to bind to CD20 expressed on Ramos cells (FIG. 9A, FIG. 9B) using flow-cytometry or recombinant EGFR (FIG. 9C, FIG. 9D) by ELISA.

Figures 10A, 10B, 10C, 10D, 10E, 10F:
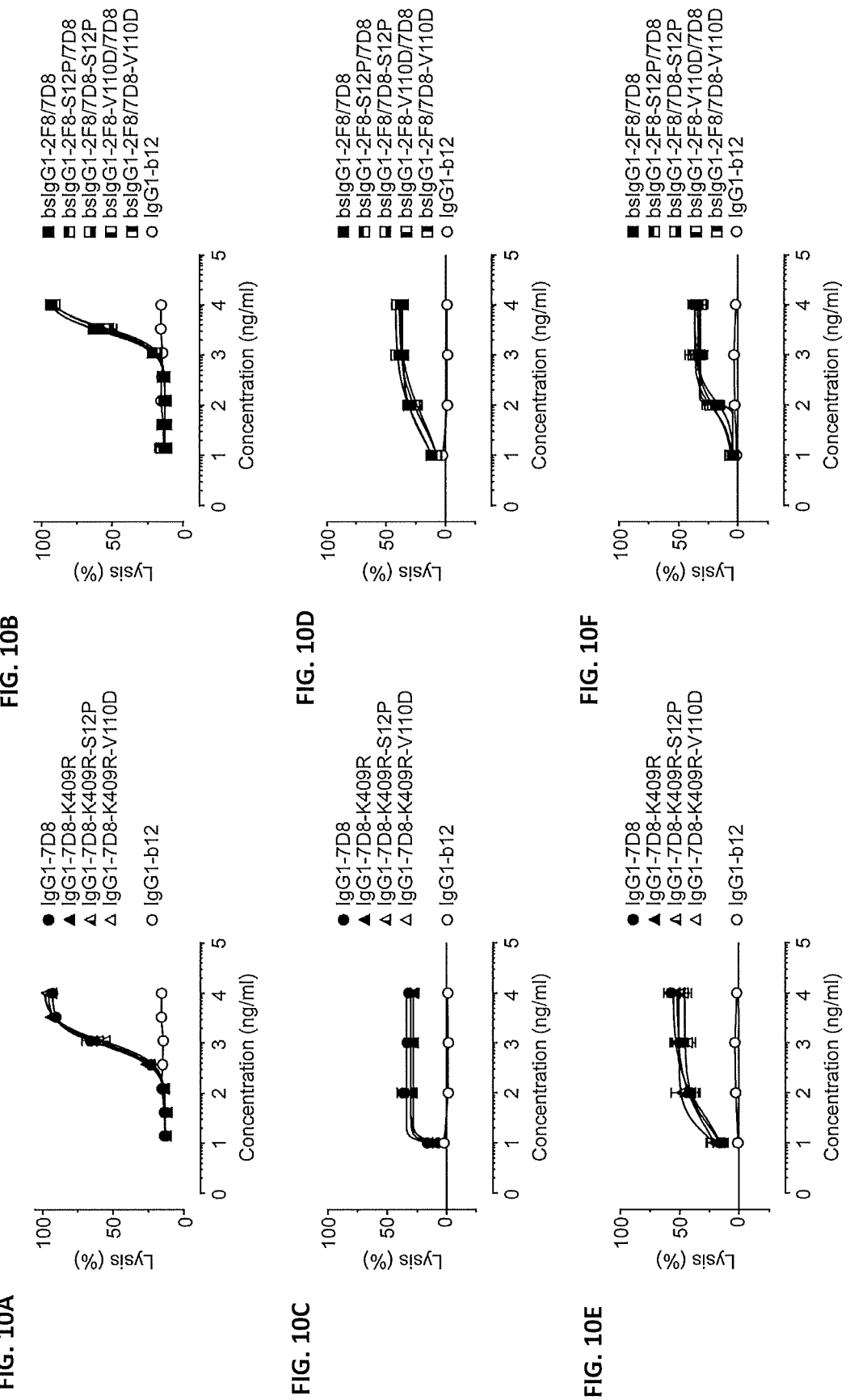

FIGS. 10A-10F: CDC- and ADCC-mediated cell kill of CD20- or EGFR-expressing cells by parental and bispecific antibodies containing the V110D or S12P mutations. Concentration series of the indicated bivalent monospecific parental antibodies (FIG. 10A, FIG. 10C, FIG. 10E) or monovalent bispecific antibodies (FIG. 10B, FIG. 10D, FIG. 10F) were used to test their capacity to mediate CDC of Daudi cells (FIG. 10A, FIG. 10B), ADCC of Daudi cells (FIG. 10C, FIG. 10D) or ADCC of A431 cells (FIG. 10E, FIG. 10F).

Figure 11A:
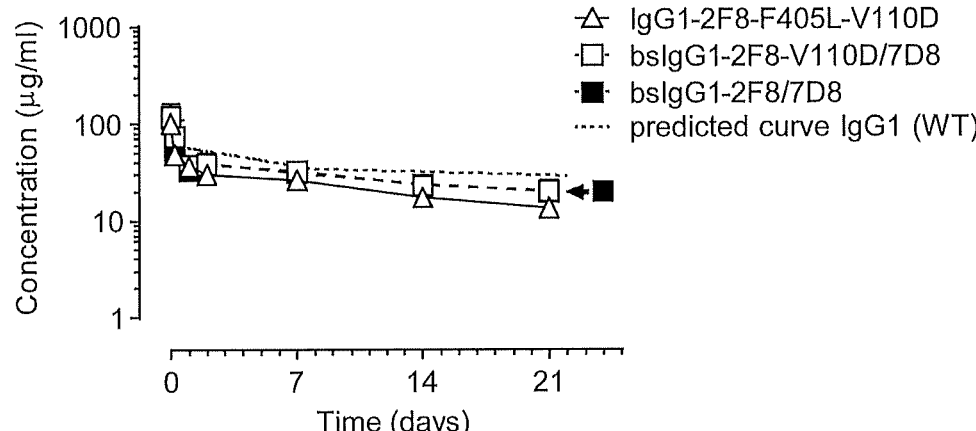
Figure 11B:
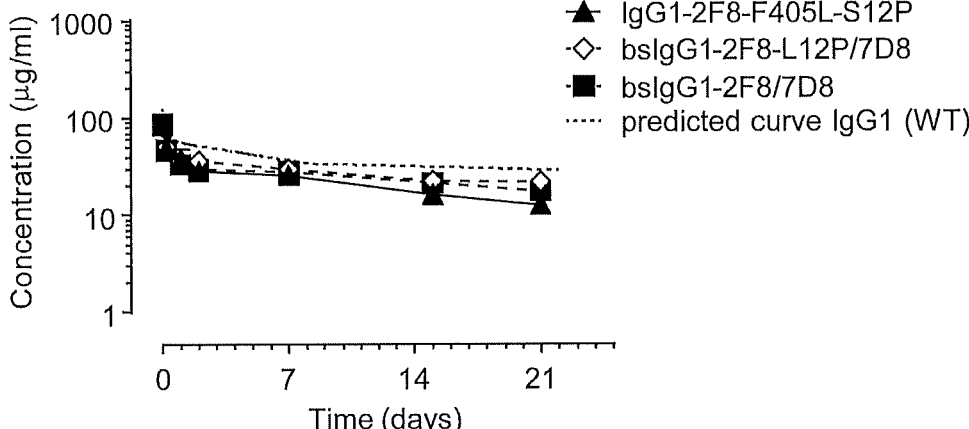
Figure 11C:
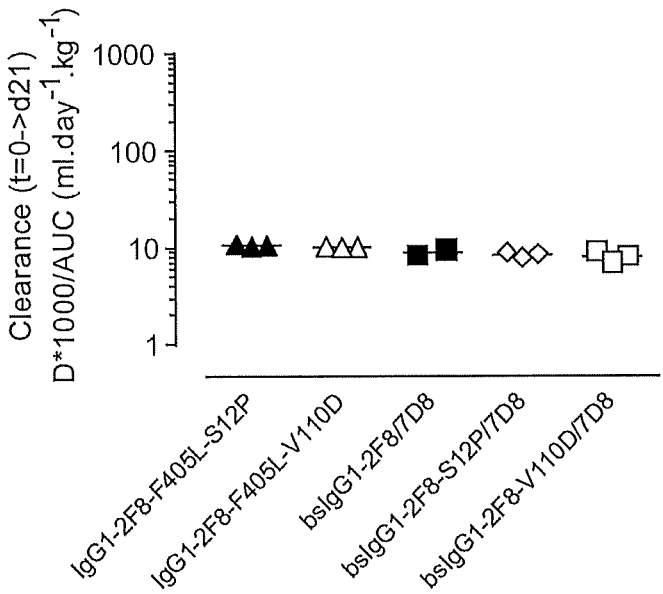

FIGS. 11A-11C: Total antibody concentration over time (FIG. 11A, FIG. 11B) and plasma clearance rate (FIG. 11C) of parental and bispecific antibodies containing the V110D (FIG. 11A) or S12P (FIG. 11B) mutation. Three groups of mice (3 mice per group) were injected with the indicated antibodies (100 μg/mice). Mean values of two ELISA experiments are shown.

DETAILED DESCRIPTION OF THE INVENTION

Definitions

The term "immunoglobulin" refers to a class of structurally related glycoproteins consisting of two pairs of polypeptide chains, one pair of light chains (LC) and one pair of heavy chains (HC), all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH) and a heavy chain constant region (CH). The heavy chain constant region typically is comprised of three domains, CH1, CH2, and CH3. The heavy chains are inter-connected via disulfide bonds in the so-called "hinge region". Each light chain typically is comprised of a light chain variable region (abbreviated herein as VL) and a light chain constant region. The light chain constant region typically is comprised of one domain, CL. The CL can be of κ (kappa) or λ (lambda) isotype.

If not stated otherwise the numbering of amino acid residues in the constant region is according to the EU-index as described in Kabat et al., Sequences of Proteins of Immunological Interest, 5th Ed. Public Health Service, National Institutes of Health, Bethesda, MD. (1991). The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)).

When used herein, the term "Fab-arm" refers to one heavy chain-light chain pair of an antibody.

When used herein, the terms "Fc region" and "Fc domain" are used interchangeably and refer to an antibody region comprising at least the hinge region, a CH2 domain and a CH3 domain (see e.g. Kabat EA, in US Department of Health and Human Services, NIH publication n° 91-3242, Edn. 5$^{th}$ edition 662, 680, 689 (1991). The Fc region may be generated by digestion of an antibody with papain, where the Fc region is the fragment obtained thereby, which includes the two CH2-CH3 regions of an immunoglobulin and a hinge region. The constant domain of an antibody heavy chain defines the antibody isotype, e.g. IgG1, IgG2, IgG3, IgG4, IgA1, IgA2, IgE. The Fc-domain mediates the effector functions of antibodies with cell surface receptors called Fc receptors and proteins of the complement system.

The term "CH2 region" or "CH2 domain" are used interchangeably and as used herein is intended to refer to the CH2 region of an immunoglobulin. Thus for example the CH2 region of a human IgG1 antibody corresponds to amino acids 228-340 according to the EU numbering system. However, the CH2 region may also be any of the other antibody isotypes as described herein.

The term "CH3 region" or "CH3 domain" are used interchangeably and as used herein is intended to refer to the CH3 region of an immunoglobulin. Thus for example the CH3 region of a human IgG1 antibody corresponds to amino acids 341-447 according to the EU numbering system. However, the CH3 region may also be any of the other antibody isotypes as described herein.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, or similar molecule.

The term "bispecific antibody" refers to an antibody having specificities for at least two different epitopes, typically non-overlapping epitopes or an antibody that contains two distinct antigen-binding sites. A bispecific antibody may be described as a heterodimeric protein whereas a mono-specific antibody may be described as a homodimeric protein. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. Fab or F(ab')2 fragments. It also should be understood that the term antibody, unless specified otherwise, also includes polyclonal antibodies, monoclonal antibodies (mAbs), antibody-like polypeptides, such as chimeric antibodies and humanized antibodies. An antibody as generated can possess any isotype.

The term "multispecific antibody" refers to an antibody having specificities for more than two different epitopes, typically non-overlapping epitopes or an antibody that contains more than two distinct antigen-binding sites. As indicated above, the term antibody herein, unless otherwise stated or clearly contradicted by the context, includes fragments of an antibody that retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody, e.g. Fab or F(ab')2 fragments. It also should be understood that the term antibody, unless specified otherwise, also includes polyclonal antibodies, monoclonal antibodies (mAbs), antibody-like polypeptides, such as chimeric antibodies and humanized antibodies. An antibody as generated can possess any isotype.

The term "full-length antibody" when used herein, refers to an antibody which contains all heavy and light chain constant and variable domains that are normally found in an antibody of that isotype.

As used herein, "isotype" refers to the immunoglobulin class (for instance IgG1, IgG2, IgG3, IgG4, IgD, IgA, IgE, or IgM) that is encoded by heavy chain constant region genes.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked by the antigen binding peptide (in other words, the amino acid residue is within the footprint of the antigen binding peptide).

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000-fold. The term "$K_D$" (M), as used herein, refers to the dissociation equilibrium constant of a particular antibody-antigen interaction.

When used herein the term "heterodimeric interaction between the first and second CH3 regions" refers to the interaction between the first CH3 region and the second CH3 region in a first-CH3/second-CH3 heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein.

An "isolated antibody", as used herein, denotes that the material has been removed from its original environment (e.g., the natural environment if it is naturally occurring or the host cell if it is recombinantly expressed). It is also advantageous that the antibodies are in purified form. The term "purified" does not require absolute purity; rather, it is intended as a relative definition, indicating an increase of the antibody concentration relative to the concentration of contaminants in a composition as compared to the starting material.

The term "host cell", as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

When used herein, the term "co-expression" of two or more nucleic acid constructs, refers to expression of the two constructs in a single host cell.

The term "tumor cell protein", as used herein, refers to a protein located on the cell surface of a tumor cell.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells, including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell. In some embodiments, an effector cell may phagocytose a target antigen or target cell.

The term "reducing conditions" or "reducing environment" refers to conditions sufficient to allow reduction of the inter-chain disulfide bonds in the hinge region of an antibody.

The term "affinity reagent" when used herein refers to a resin that contains a ligand that is immobilized on a matrix and specifically binds to surface groupings of molecules such as amino acids or sugar side chains and usually have specific three dimensional structural characteristics, as well as specific charge characteristics. Affinity reagents are tools in affinity chromatography, where purification is enabled by the specific interaction between the ligand and the product.

The term "Protein L" when used herein refers to recombinant protein L that is immobilized onto a matrix to form an affinity ligand that has affinity for a subset of the variable domain of immunoglobulin kappa light chains. For example, Protein L affinity reagents can be marketed as HiTrap™ Protein L and Capto™ L by GE Healthcare.

The term "KappaSelect" when used herein refers to a recombinant 13 kDa camelid-derived single chain antibody that is immobilized onto a matrix to form an affinity ligand that has affinity for the constant domain of human immunoglobulin kappa light chains. For example, KappaSelect affinity reagents can be marketed as KappaSelect™ by GE Healthcare.

The term "KappaXL" when used herein refers to a recombinant 13 kDa camelid-derived single chain antibody that is immobilized onto a matrix to form an affinity ligand that has affinity for the constant domain of human immunoglobulin kappa light chains. For example, KappaXL affinity reagents can be marketed as CaptureSelect™ KappaXL by Thermo Fisher.

Reference to amino acid positions in the present invention is, unless contradicted by the context, according to the EU-index as described in Kabat et al., Sequences of Proteins of Immunological Interest, 5th Ed. Public Health Service, National Institutes of Health, Bethesda, MD. (1991).

In embodiment the invention relates to a bispecific or multispecific antibody comprising a first light chain/heavy chain pair comprising a first VL and a first VH region having a first binding specificity and comprising a first light chain constant region and a first heavy chain constant region; and a second light chain/heavy chain pair comprising a second VL and a second VH region having a second binding specificity and comprising a second light chain constant region and a second heavy chain constant region, wherein the first light chain comprises a modification that reduces or eliminates binding of the first light chain to an affinity reagent. Hereby the present invention allows for the purification of the bispecific antibody species that contains only one unmodified light chain from monospecific antibodies. This can be achieved by expressing two different parental antibodies in two different systems wherein the one parental antibody is modified in the two light chains to reduce or eliminate the affinity for an affinity reagent and the other antibody is unmodified with regards to the affinity to the same affinity reagent. When a bispecific antibody is manufactured as described in WO 11/131746 the bispecific antibody can be purified from the mixture of three antibodies: a homodimeric monospecific antibody bearing two unmodified light chains, a homodimeric monospecific antibody bearing two modified light chains and a heterodimeric bispecific antibody bearing one modified light chain and one unmodified light chain. The differential properties of the three different molecules can be exploited to efficiently purify the bispecific antibody from the monospecific ones. Alternatively, when a bispecific antibody is manufactured as described in WO 11/131746, the Fab-arm exchange reaction can be performed with a molar excess of the antibody with the modified light chain to limit the levels of the homodimeric monospecific antibody bearing two unmodified light chains. The differential properties of the bispecific antibody with one modified light chain and the homodimeric monospecific antibody bearing two modified light chains can be used to purify the bispecific antibody from the monospecific antibody.

In another embodiment the two parental monospecific antibodies are both modified in the light chains but in different positions to reduce or eliminate the affinity for different affinity reagents.

The modifications of the light chains described herein can be combined with other mutations or modification of a portion of an antibody, such as the Fc domain. In a particular embodiment the homodimers are mutated in the CH3 region of the heavy chain to allow for Fab-arm exchange as described in WO 11/131746. In a preferred embodiment, one homodimer has a F405L substitution and the other homodimer has a K409R mutation in the CH3 region.

In one embodiment the affinity reagent is Protein L which has affinity for kappa light chains. HiTrap™ Protein L and Capto™ L may be obtained from GE Healthcare.

In another embodiment the affinity reagent is CaptureSelect™ KappaXL which has affinity for kappa light chains. CaptureSelect™ KappaXL may be obtained from ThermoFisher®.

In another embodiment the affinity reagent is KappaSelect™ which has affinity for kappa light chains. KappaSelect™ may be obtained from GE Healthcare.

The approach to generate bispecific antibodies described herein overcomes the disadvantages of other methods as it does not involve further mutagenesis of the Fc region but instead relies on light chain modifications which alter its binding capacity to a light chain specific affinity reagent.

In one embodiment the first light chain constant region comprises the amino acid substitution V110D, V110R, V110D, V110E, V110H, V110K, V110N, V110P, V110Q or V110W, preferably V110D or V110R, most preferred V110D. Hereby a variant is provided which has reduced or eliminated binding to the CaptureSelect-KappaXL and/or the KappaSelect resins.

In another embodiment the first light chain constant region comprises the amino acid substitution E143D. Hereby a variant is provided which has reduced binding to the KappaSelect resin.

In another embodiment the first light chain constant region comprises the amino acid substitution S12P. Hereby a variant is provided which has reduced or eliminated binding to the Protein L resin.

In another embodiment the first light chain comprises two or more of the substitutions selected from V110D, E143D and S12P. Hereby variants are provided which have eliminated or reduced binding to more than one resin type, such as to Protein L and KappaSelect.

In another embodiment the second light chain-heavy chain pair comprises a mutation in a different position than the first light chain, which mutation reduces or eliminates the binding to a different affinity reagent. This may be any affinity reagent. In one embodiment it is a light chain specific affinity reagent. In another embodiment it is a heavy chain specific affinity reagent.

In yet another embodiment the first and/or the second light chain is a kappa light chain.

In one embodiment the first and/or second light chain is a human light chain, such as human kappa light chain.

In one embodiment the invention relates to bispecific antibodies. In another embodiment the invention relates to multispecific antibodies.

In another embodiment the bispecific antibody is a human bispecific antibody and has an affinity for two different epitopes. Preferably the affinity for the epitope is independently in the micromolar, nanomolar, or picomolar range.

In one embodiment, the heavy chain of the first antibody is an IgG isotype selected from the group comprising IgG1, IgG2, IgG3 and IgG4. In one embodiment the heavy chain of the second antibody is an IgG isotype selected from the group comprising IgG1, IgG2, IgG3 and IgG4. Preferably, the isotype of the first and second antibody is the same. In one embodiment the isotype of the first and second antibody is IgG1. In another embodiment the isotype of the first and second antibody is IgG2. In another embodiment the isotype of the first and second antibody is IgG3. In another embodiment the isotype of the first and second antibody is IgG4.

In one embodiment, the antigen-binding protein is non-immunogenic or substantially non-immunogenic in a human.

In one embodiment the first and/or second light chain is a humanized light chain.

In another embodiment the invention relates to a method for producing a bispecific antibody product comprising a. providing a first antibody having a first binding specificity, said first antibody comprising two light chain/heavy chain pairs, wherein each light chain comprises a modification that reduces or eliminates binding of the light chain to an affinity reagent selected from the group consisting of Protein L, KappaXL and KappaSelect;

b. providing a second antibody having a second binding specificity, said second antibody comprising two light chain/heavy chain pairs, wherein each light chain is unmodified with respect to binding to the affinity reagent selected from the group consisting of Protein L, KappaXL and KappaSelect;

c. incubating said first and second antibodies under conditions allowing for formation of a bispecific antibody which bispecific antibody comprises:

a first light chain/heavy chain pair of said first antibody having a first binding specificity and having reduced or eliminated binding of the light chain to an affinity reagent selected from the group consisting of Protein L, KappaXL and KappaSelect;

and comprising a second light chain/heavy chain pair of said second antibody having a second binding specificity and being unmodified with respect to binding to the affinity reagent selected from the group consisting of Protein L, KappaXL and KappaSelect;

d. isolating the bispecific antibody based on the ability of the bispecific antibody to bind to the affinity reagent selected from the group consisting of Protein L, KappaXL and KappaSelect.

The affinity reagent for which the first antibody has reduced affinity should be the same affinity reagent used in the isolation step. The method can be used for bispecific or multispecific molecule that contains at least two light chains.

In one embodiment the conditions allowing for formation of a bispecific antibody is described in WO 11/131746. Preferably, these conditions are reducing conditions allowing for reduction of the inter chain disulfide bonds in the hinge region. In one embodiment the first and second antibody comprises one or more mutations in the CH3 regions which mutations are different and are such that the heterodimeric interaction between said first and second CH3 regions is stronger than each of the homodimeric interactions of said first and second CH3 regions. In one embodiment, the first antibody has an amino acid substitution at a position selected from the group consisting of: 366, 368, 370, 399, 405, 407 and 409, and said second antibody has an amino acid substitution at a position selected from the group consisting of: 366, 368, 370, 399, 405, 407 and 409, and the first and second antibody is not substituted in the same positions. In one embodiment the first antibody is substituted in position 405 and the second antibody is substituted in position 409. In a particular embodiment the first antibody has an F405L substitution. In another embodiment the second antibody has a K409R substitution.

In one embodiment the first antibody comprises a substitution in the LC of V110D and a substitution of the CH3 region of the heavy chain. In one embodiment the substitution in the CH3 region is at a position selected from the group consisting of: 366, 368, 370, 399, 405, 407 and 409. Accordingly, in one embodiment the first antibody has a V110D substitution of the LC and a substitution of the CH3 region in position 366. In another embodiment the first antibody has a V110D substitution of the LC and a substitution of the CH3 region in position 368. In another embodiment the first antibody has a V110D substitution of the LC and a substitution of the CH3 region in position 370. In another embodiment the first antibody has a V110D substitution of the LC and a substitution of the CH3 region in position 399. In another embodiment the first antibody has a V110D substitution of the LC and a substitution of the CH3 region in position 405. In another embodiment the first antibody has a V110D substitution of the LC and a substitution of the CH3 region in position 407. In another embodiment the first antibody has a V110D substitution of the LC and a substitution of the CH3 region in position 409. In another embodiment the first antibody has a V110D substitution of the LC and an F405L substitution of the CH3 region. In another embodiment the first antibody has a V110D substitution of the LC and a F405L substitution of the CH3 region and the second antibody comprises an K409R substitution. In another embodiment the first antibody has a V110D substitution of the LC and a K409R substitution of the CH3 region. In another embodiment the first antibody has a V110D substitution of the LC and a K409R substitution of the CH3 region and the second antibody comprises an F405L substitution.

In one embodiment the first antibody has a S12P substitution of the LC and a substitution of the CH3 region in position 366. In another embodiment the first antibody has a S12P substitution of the LC and a substitution of the CH3 region in position 368. In another embodiment the first antibody has a S12P substitution of the LC and a substitution of the CH3 region in position 370. In another embodiment the first antibody has a S12P substitution of the LC and a substitution of the CH3 region in position 399. In another embodiment the first antibody has a S12P substitution of the LC and a substitution of the CH3 region in position 405. In another embodiment the first antibody has a S12P substitution of the LC and a substitution of the CH3 region in position 407. In another embodiment the first antibody has a S12P substitution of the LC and a substitution of the CH3 region in position 409. In another embodiment the first antibody has a S12P substitution of the LC and an F405L substitution of the CH3 region. In another embodiment the first antibody has a S12P substitution of the LC and a K409R substitution of the CH3 region. In another embodiment the first antibody has a S12P substitution of the LC and a K409R substitution of the CH3 region and the second antibody comprises an F405L substitution. In another embodiment the first antibody has a S12P substitution of the LC and a F405L substitution of the CH3 region and the second antibody comprises a K409R substitution.

In one embodiment the first antibody has a E143D substitution of the LC and a substitution of the CH3 region in position 366. In another embodiment the first antibody has a E143D substitution of the LC and a substitution of the CH3 region in position 368. In another embodiment the first antibody has a E143D substitution of the LC and a substitution of the CH3 region in position 370. In another embodiment the first antibody has a E143D substitution of the LC and a substitution of the CH3 region in position 399. In another embodiment the first antibody has a E143D substitution of the LC and a substitution of the CH3 region in position 405. In another embodiment the first antibody has a E143D substitution of the LC and a substitution of the CH3 region in position 407. In another embodiment the first antibody has a E143D substitution of the LC and a substitution of the CH3 region in position 409. In another embodiment the first antibody has a E143D substitution of the LC and an F405L substitution of the CH3 region. In another embodiment the first antibody has a E143D substitution of the LC and a K409R substitution of the CH3 region. In another embodiment the first antibody has a E143D substitution of the LC and an F405L substitution of the CH3 region and the second antibody comprises a K409R substitution. In another embodiment the first antibody has a E143D substitution of the LC and a K409R substitution of the CH3 region and the second antibody comprises an F405L substitution.

In one embodiment the first antibody is provided in excess mass compared to the second antibody. In one embodiment first antibody is provided in at least a 1.05-fold mass excess compared to the second antibody, such as a 1.1-fold mass excess compared to the second antibody such as at least a 1.2-fold mass excess, such as at least a 1.3-fold, or 1.4-, or 1.5- or 1.6- or 1.7-fold mass excess.

In yet another embodiment the invention relates to a method for isolating a bispecific antibody, comprising isolating from a mixture of antibodies a bispecific or multispecific antibody having at least one differentially modified light chain, wherein the modification results in a bispecific antibody whose Fab-arm have a differential affinity for an affinity reagent designed for binding to the light chain of an immunoglobulin and the bispecific antibody is isolated from the mixture based on its affinity for the reagent. In one embodiment the affinity reagent is Protein L and the bispecific antibody is isolated from the mixture based on its affinity for the Protein L. In another embodiment the affinity reagent is KappaXL and the bispecific antibody is isolated from the mixture based on its affinity for the KappaXL. In another embodiment the affinity reagent is KappaSelect and the bispecific antibody is isolated from the mixture based on its affinity for the KappaSelect. In one embodiment the bispecific antibody has a modification in one of the light chains which modification is selected from V110D, E143D and S12P.

Preferably, the differentially modified light chain is non-immunogenic or substantially non-immunogenic in a human.

EXAMPLES

Example 1: Expression Vectors for the Expression of Human IgG1-2F8, Human IgG1-7D8 or Human IgG1-1014-169 and Variants with a Modified Kappa Light Chain The VH and VL coding regions of HuMab 2F8 (WO 02/100348), HuMab 7D8 (WO 04/035607) and HuMab 1014-169 (WO 12/143524) were cloned in the expression vector pConG1f (containing the genomic sequence of the human IgG1m(f) allotype constant region (Lonza Biologics)) for the production of the human IgG1 heavy chain and pConKappa (containing the human kappa light chain constant region, Lonza Biologics) for the production of the kappa light chain. Alternatively, in follow-up constructs, vectors were used containing the fully codon-optimized coding regions of the heavy chain in the pcDNA3.3 vector (Invitrogen) or the human kappa light chain of HuMab 2F8 or HuMab 7D8 in the pcDNA3.3 vector. The heavy chain constant region amino acid sequences as used were the following:

Human IgG1 heavy chain constant region (Accession number P01857)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK (SEQ ID NO: 26)

Human kappa light chain constant region (Accession number J00241)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC (SEQ ID NO: 27)

To introduce mutations in the CH3 regions of the antibody heavy chains, i.e. F405L or K409R (EU-numbering convention as described in Kabat et al., Sequences of Proteins of Immunological Interest, 5th Ed. Public Health Service, National Institutes of Health, Bethesda, MD. (1991) is used) or in the CL domains of the antibody light chains, e.g. light-chain V110D, Quickchange site-directed mutagenesis kit (Stratagene, La Jolla, CA) was used according to the manufacturer's recommendations. Alternatively the codon-optimized antibody coding regions were synthesized de novo and inserted in separate (heavy chain and light chain) pcDNA3.3 vectors.

Example 2: Antibody Production

Antibodies were produced, under serum-free conditions, by co-transfecting relevant heavy and light chain expression vectors in FreeStyle™ 293-F cells (LifeTechnologies®), using 293fectin™ (LifeTechnologies), according to the manufacturer's instructions. Alternatively, antibodies were produced, under serum-free conditions, by co-transfecting relevant heavy and light chain expression vectors in Expi293F™ cells (LifeTechnologies), using Expi-Fectamine™ 293 (LifeTechnologies), according to the manufacturer's instructions. Culture supernatants were filtered over 0.2 μm dead-end filters before analysis and purification. Alternatively, IgG1-2F8-F405L was produced as described in Gramer et al., MAbs 2013, 5:962-973.

Example 3: Antibody Quantitation in Cell Culture Samples or Chromatography Fractions Using Bio-Layer Interferometry™

The IgG concentration of cell culture samples was quantified using Bio-Layer Interferometry using Protein A biosensors with the Octet QK™ (FortéBio®). Samples were diluted 4-fold and 20-fold in Sample Diluent™ (FortéBio). The initial binding rate of each sample was measured using a read time of 60 seconds and a shaking speed 200 rpm, and the concentration was inferred by reference to a standard curve. 10 mM glycine pH 1.0 was used as a regeneration solution.

Example 4: Purification of Antibodies from Cell Culture Supernatant Using Protein a Chromatography Antibodies were purified by protein A affinity chromatography. In short, culture supernatant were loaded on 5 mL MabSelect SuRe™ columns (GE Healthcare), washed and eluted with 0.02 M sodium citrate-NaOH, pH 3. The eluate was loaded on a HiPrep™ Desalting column (GE Healthcare) immediately after purification and the antibody was exchanged into 12.6 mM $NaH_2PO_4$, 140 mM NaCl, pH 7.4 buffer (B.Braun® or Thermo Fisher®). After buffer exchange, samples were sterile filtered over 0.2 μm dead-end filters. Purity was determined by SDS-PAGE/CE-SDS and concentration was measured by absorbance at 280 nm. Purified antibodies were stored at 2-8° C. Alternatively, IgG1-2F8-F405L was purified as described in Gramer et al., MAbs 2013, 5: 962-973.

Example 5: KappaSelect Separations of Modified IgG1-2F8-F405L Variants Using Purified Proteins or Cell Culture Supernatant Four 1 mL KappaSelect (GE Healthcare) columns were joined in tandem. The columns were pre-equilibrated with Phosphate Buffered Saline (PBS; 12.6 mM sodium phosphate, 140 mM sodium chloride, pH 7.4, B.Braun or Thermo Fisher). Antibody cell culture supernatants were filtered over 0.2 μm dead-end filters and the IgG1 expression level was quantified using Bio-Layer Interferometry as described in Example 3. Between 40 mL and 80 mL of cell culture supernatant containing between 10 mg and 30 mg of unpurified IgG1-2F8-F405L variants was loaded onto the KappaSelect columns. Alternatively, 16 mg purified IgG-2F8-F405L was diluted to a total volume of 80 mL with PBS (B.Braun) and loaded onto the columns. The columns were washed with PBS, and eluted sequentially with 0.1 M Glycine HCl pH 3.0 and 0.1 M Glycine HCl pH 2.0. The eluted fractions were neutralized with a few drops of 2M Tris HCl pH 9.0, dialyzed into PBS (B.Braun) using 10 kDa molecular-weight cutoff Slide-A-Lyzer™ carriages (ThermoFisher) of the appropriate size. The column was cleaned using 6 M guanidine HCl. The flow-through fractions were combined with the PBS wash and analyzed by SDS-PAGE, as described in Example 8.

Example 6: CaptureSelect KappaXL Separations of Modified IgG1-7D8-K409R Variants from Cell Culture Supernatant or Purified Immunoglobulin Solutions A column containing approximately 1 mL of packed resin was packed manually from homogeneous CaptureSelect KappaXL (ThermoFisher) slurry into a 6.6 mm bore HiT™ column (Omnifit®), according to manufacturer's instructions. The column was pre-equilibrated with Phosphate Buffered Saline (PBS; 12.6 mM sodium phosphate, 140 mM sodium chloride, pH 7.4, ThermoFisher). Antibody cell culture supernatants were filtered over 0.2 μm dead-end filters and the IgG1 expression level was quantified using Bio-Layer Interferometry as described in Example 3. 10 mL of the supernatant, containing 1-10 mg unpurified IgG1-7D8-K409R variants, was loaded onto the CaptureSelect KappaXL column. The column was washed sequentially with approximately five column volumes of PBS and three column volumes of 0.1 M Citrate NaOH pH 5.0. Bound material was eluted with 0.1 M Citrate NaOH pH 3.5. Fractions of 1 mL were neutralized with a few drops of 2 M Tris HCl pH 9.0. The column was washed with 6M Guanidine HCl. The flow-through was pooled with the PBS wash. Fractions that contained significant absorption at 280 nm peak from either the pH 5.0 wash or the pH 3.5 elution were pooled. The load, pooled flow-through and pooled fractions were analyzed using Bio-Layer Interferometry and CE-SDS, as described in Examples 3 and 9.

Example 7: Protein L Separations of Modified IgG1-2F8-F405L Variants with Modified Kappa Light Chain Variable Domains A 5 mL HiTrap Protein L Column (GE Healthcare) was pre-equilibrated with Phosphate Buffered Saline (PBS; 12.6 mM sodium phosphate, 140 mM sodium chloride, pH 7.4). Antibody cell culture supernatants containing IgG-2F8-F405L-R18P, IgG-2F8-F405L-T20S-T22S, IgG-2F8-F405L-R24S or IgG-2F8-F405L-K107L were filtered over 0.2 μm dead-end filters and the IgG1 expression level was quantified using Bio-Layer Interferometry as described in Example 3. 10 mL of the supernatant was loaded onto the HiTrap Protein L column. Alternatively, antibody culture supernatants were purified by Protein A chromatography, as described in Example 4. Between 0.8 mg and 2.8 mg of purified IgG-2F8-F405L, IgG-2F8-F405L-S9L or IgG-2F8-F405L-S12P were mixed to a total volume of 10 mL in PBS and loaded onto the HiTrap Protein L column. The column was washed with PBS and specifically bound material was eluted sequentially with 0.1 M glycine-HCl pH 3.5, 3.0 and 2.5 and neutralized with a few drops of 2M Tris pH 9.0. The column was washed using 15 mM sodium hydroxide. The material in the flow-through was analyzed using Bio-Layer Interferometry and CE-SDS, as described in Examples 3 and 9.

Example 8: Analysis of Samples of Chromatography Flow-Through Fractions Using Sodium Dodecyl Sulfate-Polyacrylamide Gel Electrophoresis (SDS-PAGE)

Samples were mixed with equal amounts of NuPAGE LDS™ Sample Buffer (Invitrogen®) and heated at 70° C.

for 10 minutes. SDS-PAGE was performed under non-reducing conditions on 4-12% NuPAGE™ Bis-Tris gels (Invitrogen) using a modified Laemmli method (Laemmli 1970 Nature 227(5259): 680-5), with 1× NuPAGE™ MOPS SDS Running Buffer (Invitrogen). The SDS-PAGE gels were stained with Coomassie™ stain and digitally imaged using an OptiGo™ imaging system (Isogen Life Sciences®). SeeBlue Plus2™ Pre-stained Standard was used as a molecular weight standard (Invitrogen).

Example 9: Analysis of Samples of Chromatography Fractions Using Capillary Electrophoresis—Sodium Dodecyl Sulfate (CE-SDS)

Samples were filtered over 0.2 μm dead-end filters before analysis. Sample concentrations were adjusted by diluting in PBS such that the concentration was not greater than 250 ug/mL, using the Bio-Layer Interferometry concentration measurement described in Example 3 or based upon the absorption at 280 nm. CE-SDS was performed using a LabChip GXII™ (Caliper Life Sciences®, MA) on a HT Protein Express LabChip (Caliper Life Sciences, MA) under non-reducing conditions according to manufacturer's instructions. Data were analysed using LabChipGX software V3.1™ (Caliper Life Sciences, MA).

Example 10: Identification of Knock-Out Mutations for the CaptureSelect LC-Kappa (Hu) Affinity Matrix As described by the manufacturer, the CaptureSelect LC-kappa (Hu) affinity matrices, KappaSelect and Capture-Select KappaXL (GE-Healthcare, BAC®), both contain a 13 kDa Llama antibody fragment recognizing a unique epitope on the constant part of the human kappa L chain (CL). Furthermore, according to the manufacturer, the fragment is cross-reactive with non-human primate species and non-cross-reactive with mouse, rabbit, bovine and rat L chains or with human lambda L chains.

Sequence alignment of the kappa CL domain of these different species revealed several amino acid residues that were conserved in human and primate kappa sequences, but different in the other sequences. Of these, residues exposed in the complex of light and heavy chain were selected for analysis and human kappa L chains were designed containing the mouse (mm)CL domain or single point-mutations corresponding with their mouse-specific counterparts (Table 1). An additional point-mutation (F135L) was introduced into the mmCL domain to facilitate efficient pairing with human H-chains.

Figure 3A:
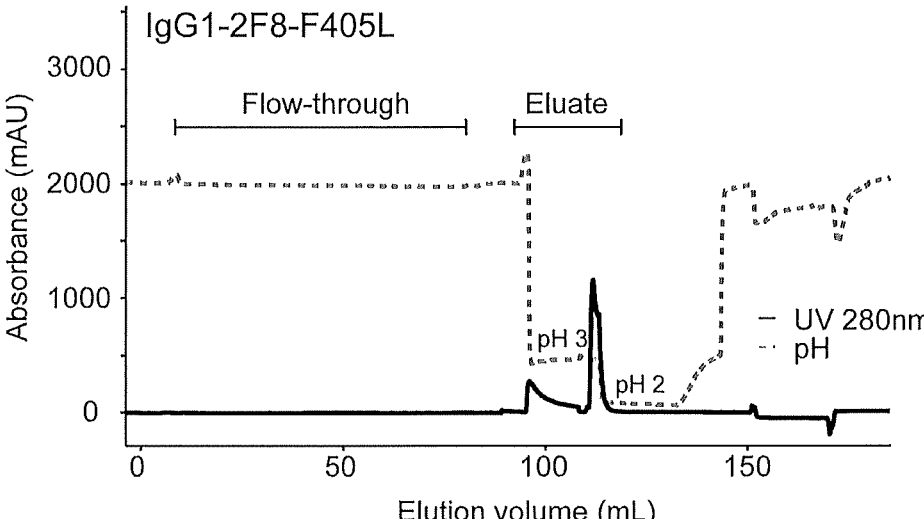
FIGS. 3A-3F: Exemplary KappaSelect purifications of modified IgG1-2F8-F405L variants using purified protein (FIG. 3A) IgG1-2F8-F405L, or cell culture supernatants containing produced (FIG. 3B) IgG1-2F8-F405L-mmF135L, (FIG. 3C) IgG1-2F8-F405L-V110D, (FIG. 3D) IgG1-2F8-F405L-E143D and (FIG. 3E) IgG1-2F8-F405L-E165D. The absorption at 280 nm (solid line) and pH (dashed grey line) were monitored. The purifications from cell culture supernatant show an elevated absorption during column loading from non-bound material in the flow-through. Specifically bound IgG1-2F8-F405L variants were eluted at pH 3.0 and pH 2.0 and detected by peaks in the absorption at 280 nm.
Figure 3B:
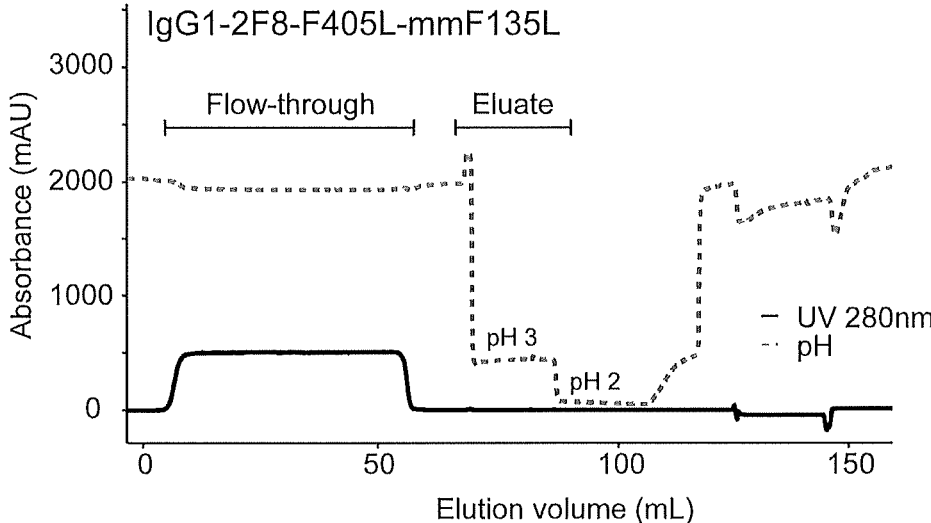
Figure 3C:
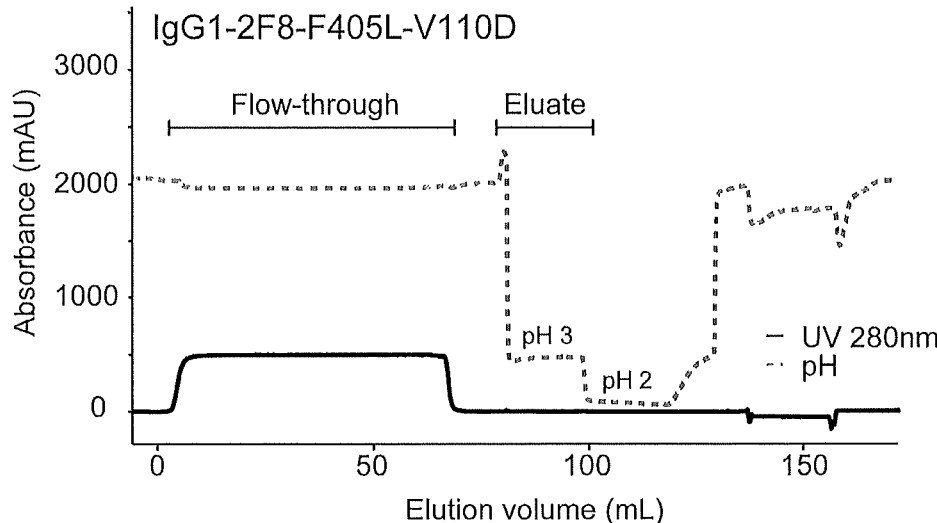
Figure 3D:
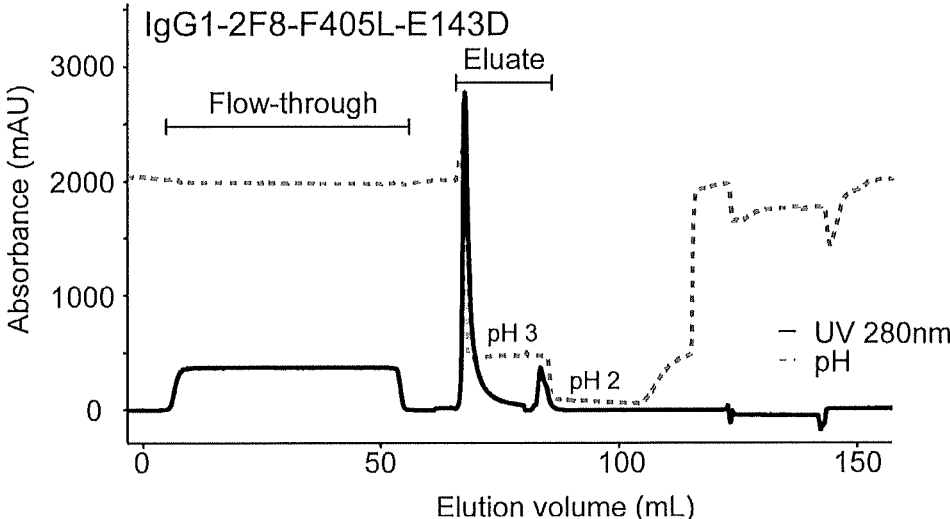
Figure 3E:
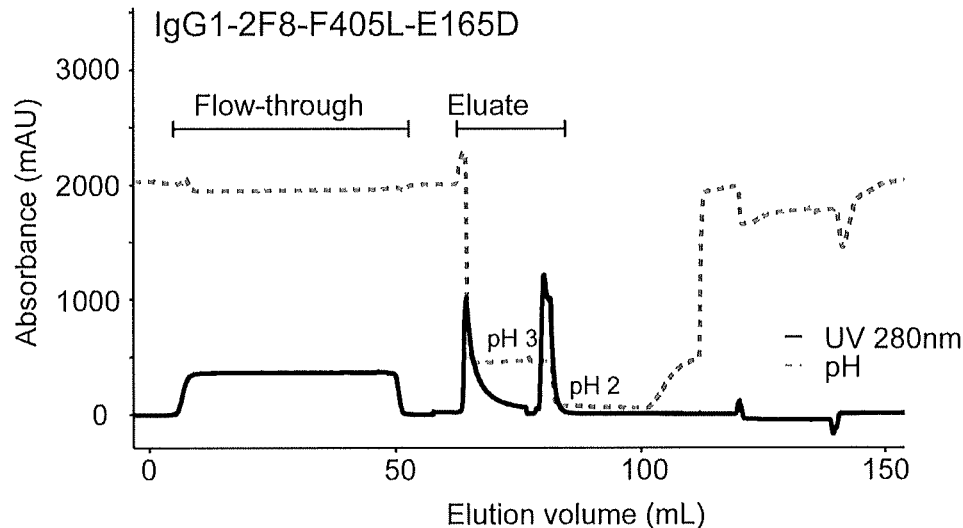
Figure 3F:
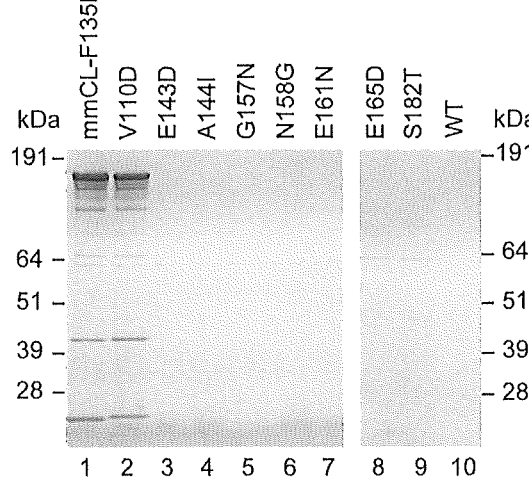
Figure 4A:
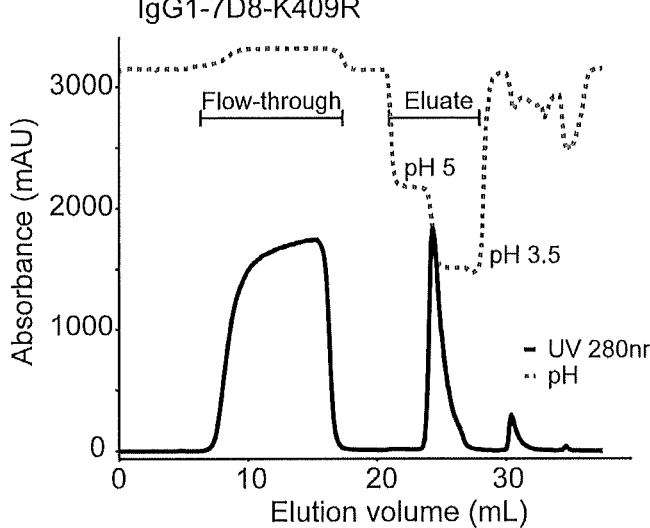
FIGS. 4A-4F: Exemplary CaptureSelect KappaXL separations of Modified IgG1-7D8-K409R variants from cell culture supernatants containing produced (FIG. 4A) IgG1-7D8-K409R, (FIG. 4B) IgG1-7D8-K409R-V110D, (FIG. 4C) IgG1-7D8-K409R-V110K, (FIG. 4D) IgG1-7D8-K409R-V110D, (FIG. 4E) IgG1-7D8-K409R-V110E, (FIG.
Figure 4B:
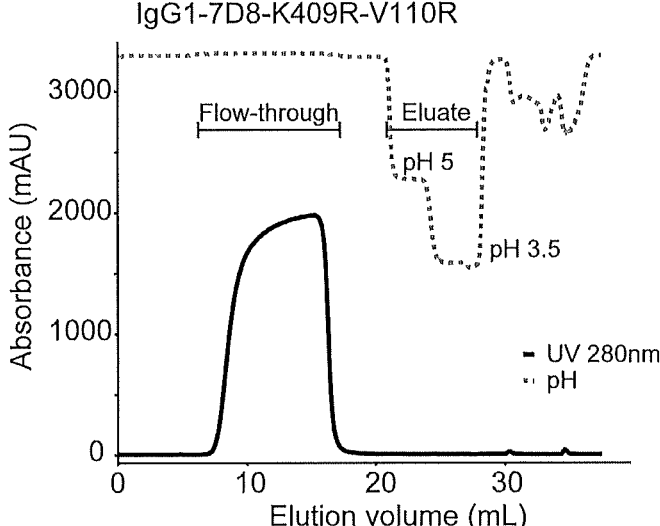
Figure 4C:
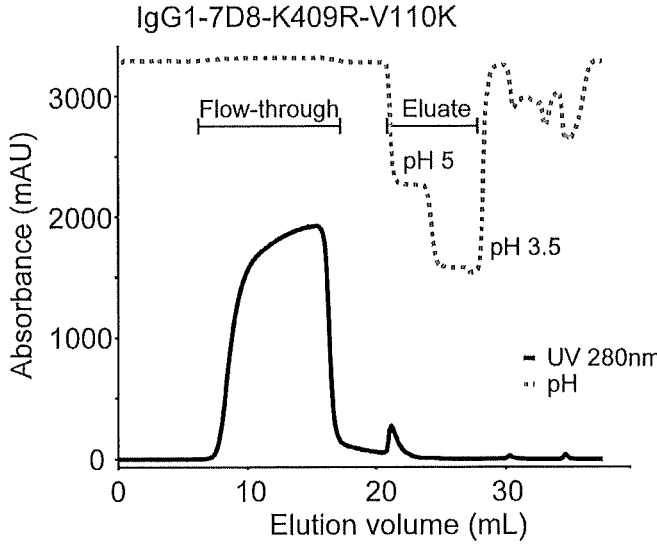
Figure 4D:
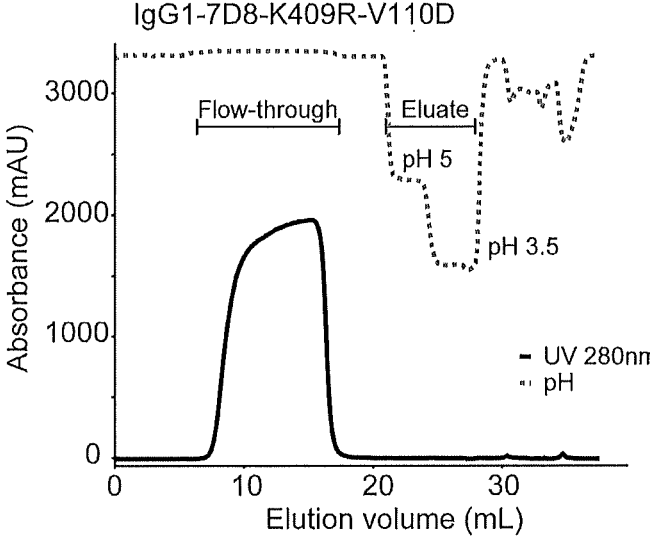
Figure 4E:
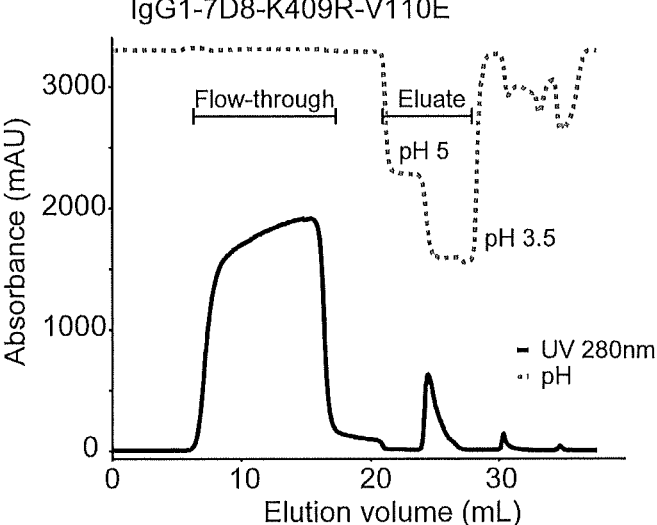
Figure 4F:
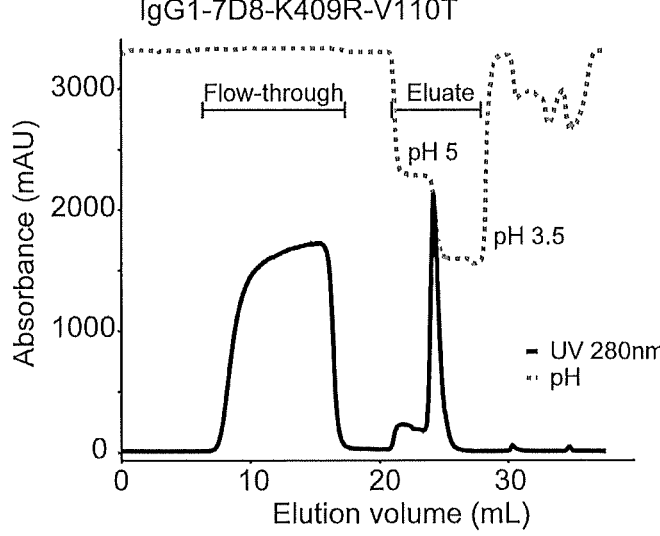

Nine kappa L-chain mutants were expressed in combination with the appropriate H-chains and assessed for their ability to bind to KappaSelect resin (as described in Example 5). Purified IgG1-2F8-F405L was used as a positive control for affinity purifications using KappaSelect resin (FIG. 3A). As expected, the IgG1-2F8-F405L containing the mmCL(F135L) L-chain, could not be purified by KappaSelect resins (FIG. 3B). With the exception of V110D, all mutants could still be purified, suggesting that V110 in the kappa LC is directly or indirectly part of the KappaSelect binding site (FIG. 3). IgG1-2F8-F405L-E143D predominantly elutes at a higher pH than the other mutants, which is indicative of a weaker interaction with the column resin (FIG. 3D). The effects of the single point mutations on binding to the KappaSelect resin are summarized in Table 2, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

The tolerability of the CaptureSelect KappaXL affinity matrix for substitutions in residue V110 of the kappa L-chain was further assessed by purifying (as described in Example 6) individually expressed kappa L-chain mutants, in combination with the appropriate H-chain, that contained substitutions at position V110 to all natural amino acids (except C). As expected, IgG1-7D8-K409R bound to the resin since an elution peak at 280 nm is detected during the pH 3.5 elution. The V110D substitution abrogated binding to the KappaSelect resin also prevented binding to CaptureSelect KappaXL binding, suggesting that both matrices bind to the same or similar epitopes. V110R was the only other mutation that showed no detectable interaction with the resin under these conditions (FIGS. 4 and 5). Other IgG1-7D8-K409R variants show a reduced affinity for the resin. For example IgG1-7D8-K409R-V110E is detected in the pH 3.5 eluate and flow-through fractions, IgG1-7D8-K409R-V110K is detected in the pH 5.0 wash and flow-through fractions, and IgG1-7D8-K409R-V110T elutes during both the pH 5.0 wash and pH 3.5 elution (FIGS. 4 and 5). The effects of the single point mutations on binding to the CaptureSelect KappaXL resin are summarized in Table 3, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

Example 11: Identification of Knock-Out Mutations for the Protein L Affinity Matrix Protein L has also been described to bind to the variable portion of kappa subtypes I, III and IV but not to kappa subtype II or most lambda subtypes (Nilson et al. J Biol Chem. 1992; 267(4):2234-9). Furthermore, the epitope of protein L on human and murine kappa lights chains has been identified by X-ray crystallography (Graille et al. Structure. 2001 9(8):679-87; Graille et al. Biol Chem. 2002 277(49): 47500-6). Analysis of these crystal structures identifies 17 residues as being important contact residues in both structures (FIG. 2). Of these, 7 residues were selected based upon analysis of the structures and sequence alignments and were mutated to residues commonly found at the equivalent position in either the kappa subtype II or most lambda subtype I sequences using single or double point mutations (FIG. 2, Table 1).

These kappa L-chain mutants were expressed in combination with the appropriate H-chains and assessed for their ability to bind to Protein L resin (as described in Example 7). The purified IgG1-2F8-F405L positive control and most of the mutated proteins were bound by the resin. In contrast, IgG1-2F8-S12P does not bind to the resin under these conditions (FIG. 6). The effects of the point mutations on binding to the HiTrap Protein L column are summarized in Table 4, where (+++) indicated a binding profile similar to the positive control; (++) indicates a greater proportion of IgG1 eluting at higher pH, compared with the control; (+) indicates significant IgG1 protein detected in the flow-through and PBS wash and (−) indicates no binding detected to the resin.

Example 12: Generation of Bispecific Antibodies that Include Matching Mutations F405L and K409R by Controlled Fab-Arm Exchange Bispecific antibodies were generated in vitro using the DuoBody® platform technology, i.e. controlled Fab-arm exchange (cFAE) or 2-MEA-induced Fab-arm exchange as described in WO 2011/147986; Labrijn et al., PNAS 2013, 110: 5145-50; Gramer et al., MAbs 2013, 5: 962-973 and Labrijn et al., Nat Protoc 2014, 9: 2450-63). The reaction conditions used in this method were optimized for human IgG1-derived bispecific antibodies and were dependent on determinants in the hinge region and the CH3 region (Labrijn et al., J Immunol 2011, 187: 3238-46; Labrijn et al., PNAS 2013, 110: 5145-50).

To generate bispecific antibodies, a 1.3-fold mass excess of IgG1-2F8-F405L-V110D was mixed with IgG1-7D8-K409R or IgG1-1014-169-K409R and incubated with a final concentration of 75 mM 2-mercaptoethylamine-HCl (2-MEA) in PBS (B.Braun or ThermoFisher) at 31° C. for 5 hours. Reactions were performed on a scale of 4.5 mg to 50 mg and final concentration of 2 mg/mL to 5 mg/mL of total IgG. The reaction was stopped when the reducing agent 2-MEA was removed by dialysis into PBS (B.Braun or ThermoFisher) using 10 kDa molecular-weight cutoff Slide-A-Lyzer carriages (ThermoFisher) of the appropriate size. The dialysis buffer was refreshed until the theoretical concentration of 2-MEA was less than 50 μM. The final Duo-Body™ samples were filtered over 0.2 μm dead-end filters and the absorbance at 280 nm (A280) of bispecific products was measured to determine the final concentration. Samples were stored at 2-8° C. for at least 24 hours before further use.

Example 13: Separation of Asymmetrically Modified Bispecific Antibodies Mixtures Using CaptureSelect KappaXL Resin A column containing approximately 1 mL of packed resin was packed manually from homogeneous CaptureSelect KappaXL slurry into an Omnifit 6.6 mm bore HiT column, according to manufacturer's instructions. The column was pre-equilibrated with Phosphate Buffered Saline (PBS; 12.6 mM sodium phosphate, 140 mM sodium chloride, pH 7.4; ThermoFisher). The reaction product of a DuoBody exchange reaction of IgG1-2F8-F405L-V110D with IgG1-7D8-K409R was prepared as described in Example 12. Between 2.3 mg and 10 mg sample was loaded onto the CaptureSelect KappaXL column. The column was washed with PBS (ThermoFisher). Elution was performed sequentially with 0.1 M Glycine HCl pH 4.0, 0.1 M Glycine HCl pH 3.5 and 0.1 M Glycine HCl pH 3.0. Alternatively, the column was washed with 0.1 M sodium citrate-NaOH pH 5.0 and eluted with 0.1 M sodium citrate-NaOH pH 3.5. The column was washed with 6M Guanidine HCl. Fractions that contained significant absorption at 280 nm peak during the pH 3.5 elution were neutralized with a few drops of 2 M Tris HCl pH 9.0, pooled and dialyzed to PBS (ThermoFisher). The load and eluate fractions were analyzed using analytical hydrophobic interaction chromatography and HP-SEC as described in Examples 7, 15 and 17.

Example 14: Separation of Asymmetrically Modified Bispecific Antibodies Mixtures Using Protein L Resin A 5 mL HiTrap Protein L column (GE Healthcare) was pre-equilibrated with Phosphate Buffered Saline (PBS; 12.6 mM sodium phosphate, 140 mM sodium chloride, pH 7.4; ThermoFisher or BBraun). The reaction product of a Duo-Body exchange reaction of IgG1-2F8-F405L-S12P with IgG1-1014-169-K409R was prepared as described in Example 12. Approximately 4 mg of the reaction product was loaded onto the Protein L column. The column wash washed sequentially with PBS (ThermoFisher or BBraun) and 0.02 M sodium citrate-NaOH, pH 5. Elution was performed sequentially with 0.1 M Glycine HCl pH 3.5, 0.1 M Glycine HCl pH 3.0 and 0.1 M Glycine HCl pH 2.5. Alternatively, elution was performed sequentially with 0.02 M sodium citrate pH 5 and 0.1 M Glycine HCl pH 3.0 The column was washed with 0.015 M NaOH. Fractions that contained significant absorption at 280 nm peak during the pH 3.5 or pH 3.0 elution were neutralized with a few drops of 2 M Tris HCl pH 9.0, pooled and dialyzed to PBS (ThermoFisher or BBraun). The load and eluate fractions were analyzed using analytical cation exchange chromatography, HP-SEC and CE-SDS as described in Examples 7, 16 and 17.

Example 15: Quantitation of Bispecific Antibody Content Using Analytical Hydrophobic Interaction Chromatography High Pressure Liquid Chromatography (HPLC)—hydrophobic interaction chromatography (HIC) was used to separate both parental antibodies from the bispecific antibody product, based on their hydrophobic properties. Parental antibodies and analysis samples normalized in concentration and diluted two-fold with HIC eluent A (15.4 mM $K_2HPO_4$, 9.6 mM $KH_2PO_4$, 1,5 M $(NH_4)_2SO_4$; pH 7.0). The IgG molecules with different hydrophobic properties were separated by using a Butyl-NPR, 2.5 μm, 4.6×35 mm HIC-HPLC column (Tosoh Bioscience) with a flow rate of 1 mL/min. 50 μL of sample was injected and elution was performed with a 12-min gradient of HIC eluent A (15.4 mM $K_2HPO_4$, 9.6 mM $KH_2PO_4$, 1,5 M $(NH_4)_2SO_4$; pH 7.0) to HIC eluent B (15.4 mM $K_2HPO_4$, 9.6 mM $KH_2PO_4$; pH 7.0) with detection at 280 nm. Empower 3 software (Waters) was used to assign and integrate peak areas. Chromatograms of the parental antibodies were used as reference to identify their position in the end-product.

Example 16: Quantitation of Bispecific Antibody Content Using Analytical Cation Exchange Chromatography High Pressure Liquid Chromatography (HPLC)—analytical cation exchange chromatography (CIEX) was used to separate both parental antibodies from the bispecific antibody product, based on their charged properties. Parental antibodies and analysis samples at 1 mg/mL in mobile Phase A (10 mM NaPO4, pH 7.0) were injected onto the HPLC. The differently charged IgG molecules were separated by using a ProPac WCX-10, 4 mm×250 mm, analytical column with a flow rate of 1 mL/min. 50 μL of sample was injected and elution was performed with a gradient of Mobile Phase A (10 mM NaPO4, pH 7.0) to Mobile Phase B (10 mM NaPO4, pH 7.0, 0.25 M NaCl) with detection at 280 nm. Empower 3 software (Waters) was used to assign and integrate peak areas. Chromatograms of the parental antibodies were used as reference to identify their position in the end-product.

Example 17: Quantitation of Antibody Monomer Content Using HP-SEC

HP-SEC fractionation was performed using a Waters Alliance 2695™ separation unit (Waters®, Etten-Leur, The Netherlands) connected to a TSK HP-SEC™ column (G3000SWxl; Tosoh Biosciences®, via Omnilabo, Breda, The Netherlands) and a Waters 2487™ dual λ absorbance detector (Waters). The samples were run at 1 mL/min. Results were processed using Empower™ software version 2002 and expressed per peak as percentage of total peak height.

Example 18: Melting Temperature Determination Using Differential Scanning Flurimetry Differential scanning fluorimetry measurements were performed to determine the midpoint (temperature) of unfolding (melting point, Tm). Sypro Orange™ dye (SYPRO Orange protein gel stain (5000× concentrate in DMSO), Invitrogen) was diluted 325-fold in PBS. Antibody samples were diluted to 1 mg/mL in PBS and 5 μL of the diluted sample was added to 20 μL diluted Sypro Orange in iCycler iQ™ 96-well PCR plates. Fluorescence was measured on a Bio-Rad CFX96 Deep Well Real-Time™ system detection system upon incubation at increasing temperature from 25° C. to 95° C. in increments of 0.5° C. (Excitation 485 nm, Emission 575 nm). The data was analyzed using Bio-Rad CFX Manager Software 3.1™ and melting points were determined from the fluorescence versus temperature graphs by the software.

Figure 7A:
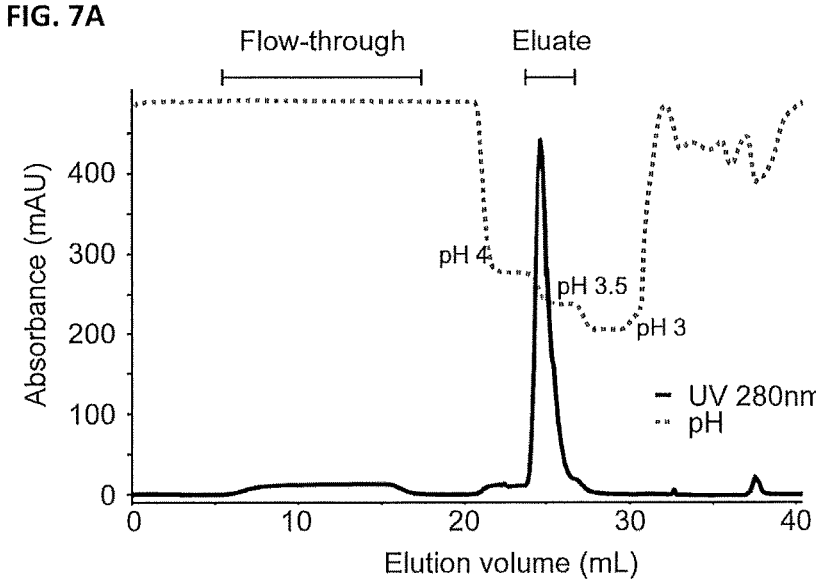
Figure 7D:
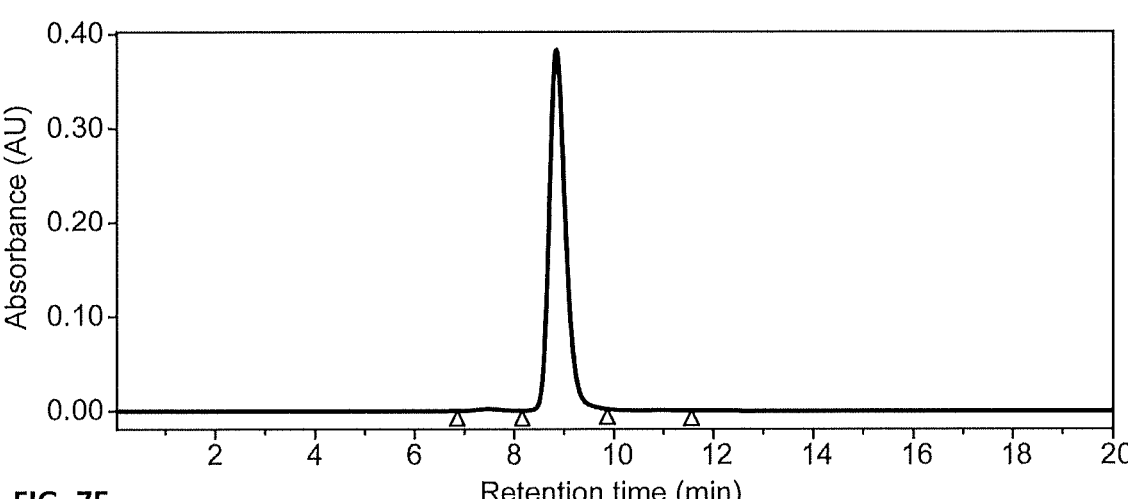
Figure 7E:
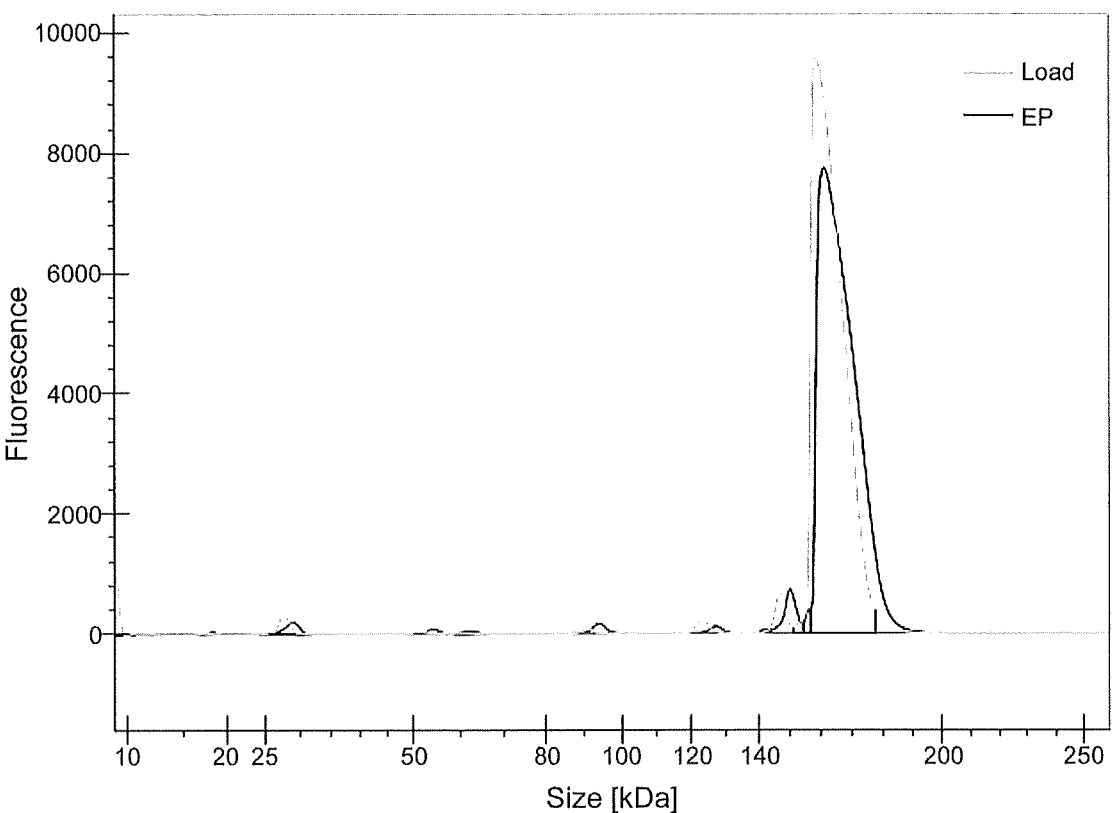
Figure 8A:
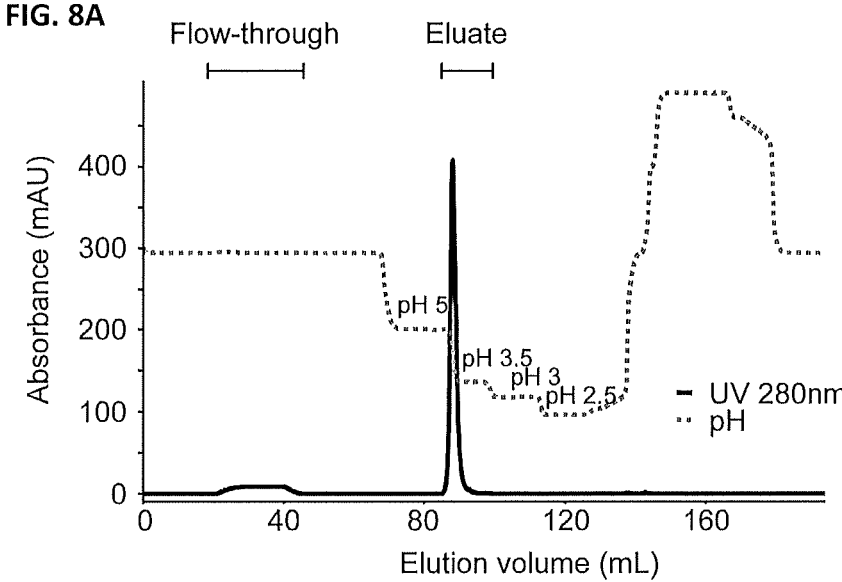
Figures 8B, 8C:
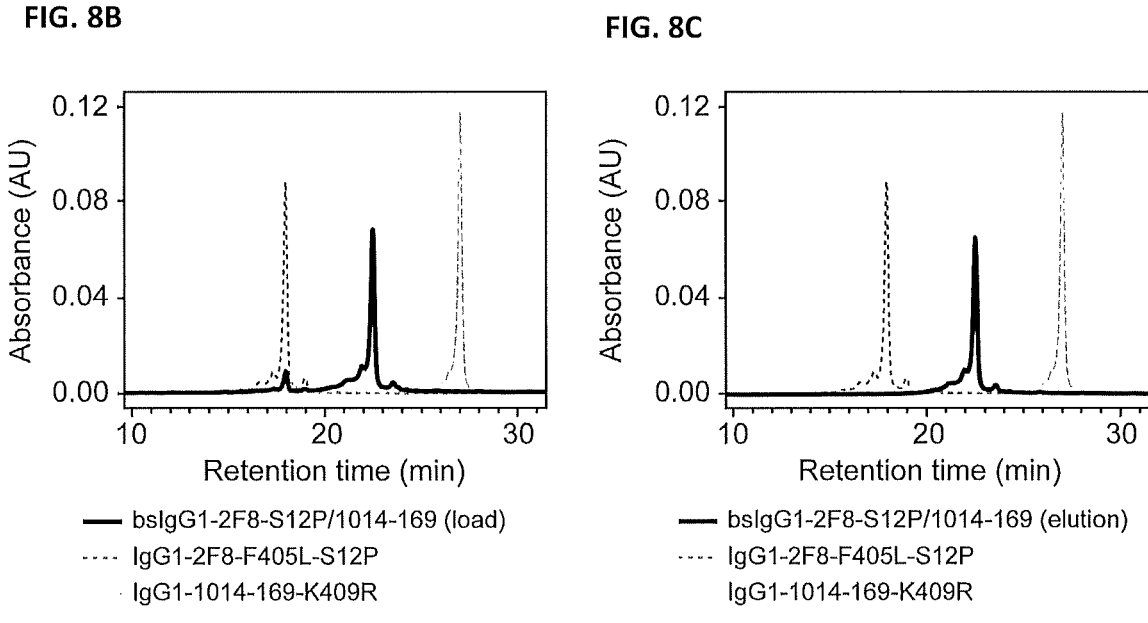
Figure 8D:
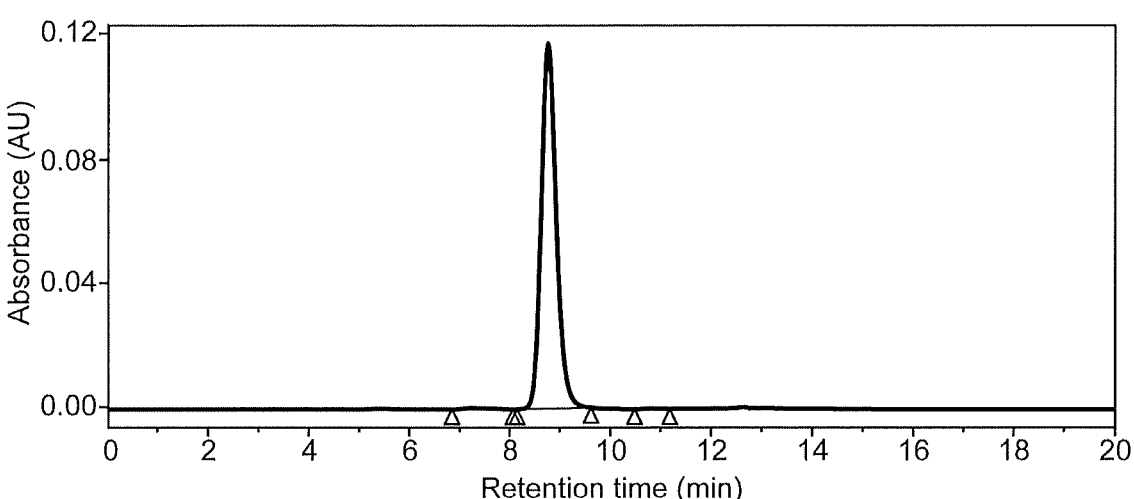
Figure 8E:
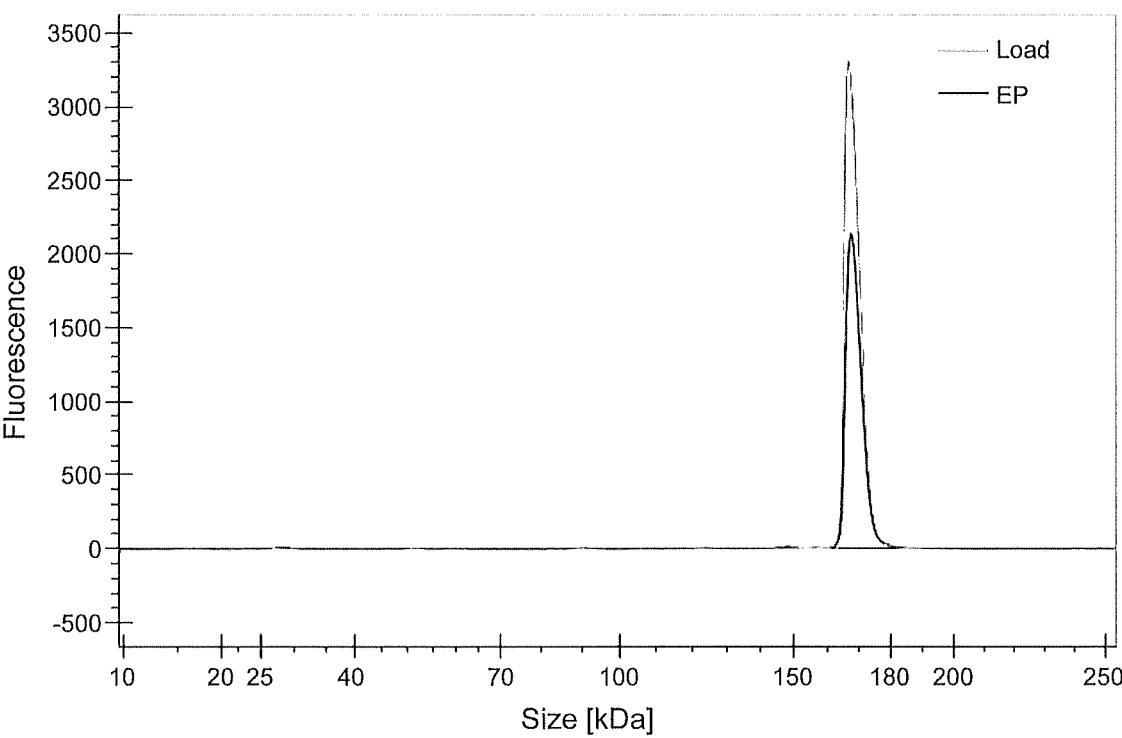

FIGS. 7 and 8 show that a single step purification using CaptureSelect KappaXL resin or HiTrap Protein L resin can separate bispecific antibodies from residual parental antibodies. The purification of the reaction product of a 1.3:1 exchange of IgG1-2F8-F405L-V110D×IgG1-7D8-K409R on CaptureSelect KappaXL resin showed a sharp elution peak (FIG. 7A) that contained >98% bispecific antibody (FIG. 7B,C). Similarly, the purification of the reaction product of a 1.3:1 exchange of IgG1-2F8-F405L-S12P× IgG1-1014-169-K409R on Protein L resin showed a sharp elution peak (FIG. 8A) that contained >98% bispecific antibody (FIG. 8B,C). The end product from both purifications contained <1% multimers (FIGS. 7D,E, 8D,E), showing that neither the DuoBody exchange reaction nor the polishing induce aggregation or fragmentation. The S12P and V110D point mutations do not affect thermal melting temperatures, as inferred from differential scanning fluorimetry measurements (Table 5).

Example 19: Binding of S12P and V110D Containing Antibodies to CD20-Expressing Cells or Recombinant EGFR Binding of antibodies IgG1-7D8, IgG1-7D8-K409R, IgG1-7D8-K409R-S12P and IgG1-7D8-K409R-V110D (CD20-specific), IgG1-2F8, IgG1-2F8-F405L, IgG1-2F8-F405L-V110D and IgG1-2F8-F405L-S12P (EGFR-specific), and bispecific (bs)IgG1-2F8/7D8, bsIgG1-2F8-S12P/7D8, bsIgG1-2F8/7D8-S12P, bsIgG1-2F8-V110D/7D8 and bsIgG1-2F8/7D8-V110D to CD20-positive Ramos cells or recombinant EGFR was analyzed by FACS analysis or ELISA, respectively.

For the FACS, cells ($1×10^5$ cells/well) were incubated in polystyrene 96-well round-bottom plates (Greiner bio-one 650101) with serial dilutions of antibody preparations (range 14 to 10000 ng/mL in 3-fold dilutions) in 100 μL PBS/0.1% BSA/0.02% azide at 4° C. for 30 min. After washing twice in PBS/0.1% BSA/0.02% azide, cells were incubated in 100 μL with secondary antibody at 4° C. for 30 min. As a secondary antibody, R-Phycoerythrin (PE)-conjugated goat-anti-human IgG F(ab')2 (109-116-098, Jackson ImmunoResearch Laboratories, Inc.®, West Grove, PA) diluted 1/100 in PBS/0.1% BSA/0.02% azide, was used for all experiments. Next, cells were washed twice in PBS/0.1% BSA/0.02% azide, resuspended in 150 µL PBS/0.1% BSA/0.02% azide and analyzed on a FACS Canto II™ (BD Biosciences). For the ELISA, 96-well ELISA plates (Greiner bio-one®, Frickenhausen, Germany) were coated overnight with 2 µg/mL (100 µL/well) of recombinant extracellular domain of EGFR in PBS at 4° C. The plates were washed once with PBST. Dilution series of the antibody samples (range 14 to 10000 ng/mL in 3-fold dilutions) in PBST/0.2% BSA (PBSTB) were transferred to the coated ELISA plates (100 µL/well) and incubated on a plate shaker (300 rpm) for 60 min at room temperature (RT). Samples were discarded and the plates were washed once with PBS/0.05% Tween 20 (PBST). Next, the plates were incubated on a plate shaker (300 rpm) with an HRP-conjugated goat anti-human IgG (Fc) (109-035-098, Jackson ImmunoResearch Laboratories, Westgrove, PA, USA) diluted 1:5.000 in PBSTB (100 µL/well) for 60 min at RT. The plates were washed once with PBS/0.05% Tween 20 (PBST). ABTS (50 mg/mL; Roche Diagnostics GmbH®, Mannheim, Germany) was added (100 µL/well) and incubated protected from light for 30 min at RT. The reaction was stopped with 2% oxalic acid (100 µL/well; Riedel de Haen Seelze®, Germany). After 10 min at RT, absorbance at 405 nm was measured in an ELISA plate reader. Binding curves were analyzed using non-linear regression (sigmoidal dose-response with variable slope) using GraphPad Prism V5.04™ software (GraphPad Software®, San Diego, CA, USA).

Figures 9A, 9B, 9C, 9D:
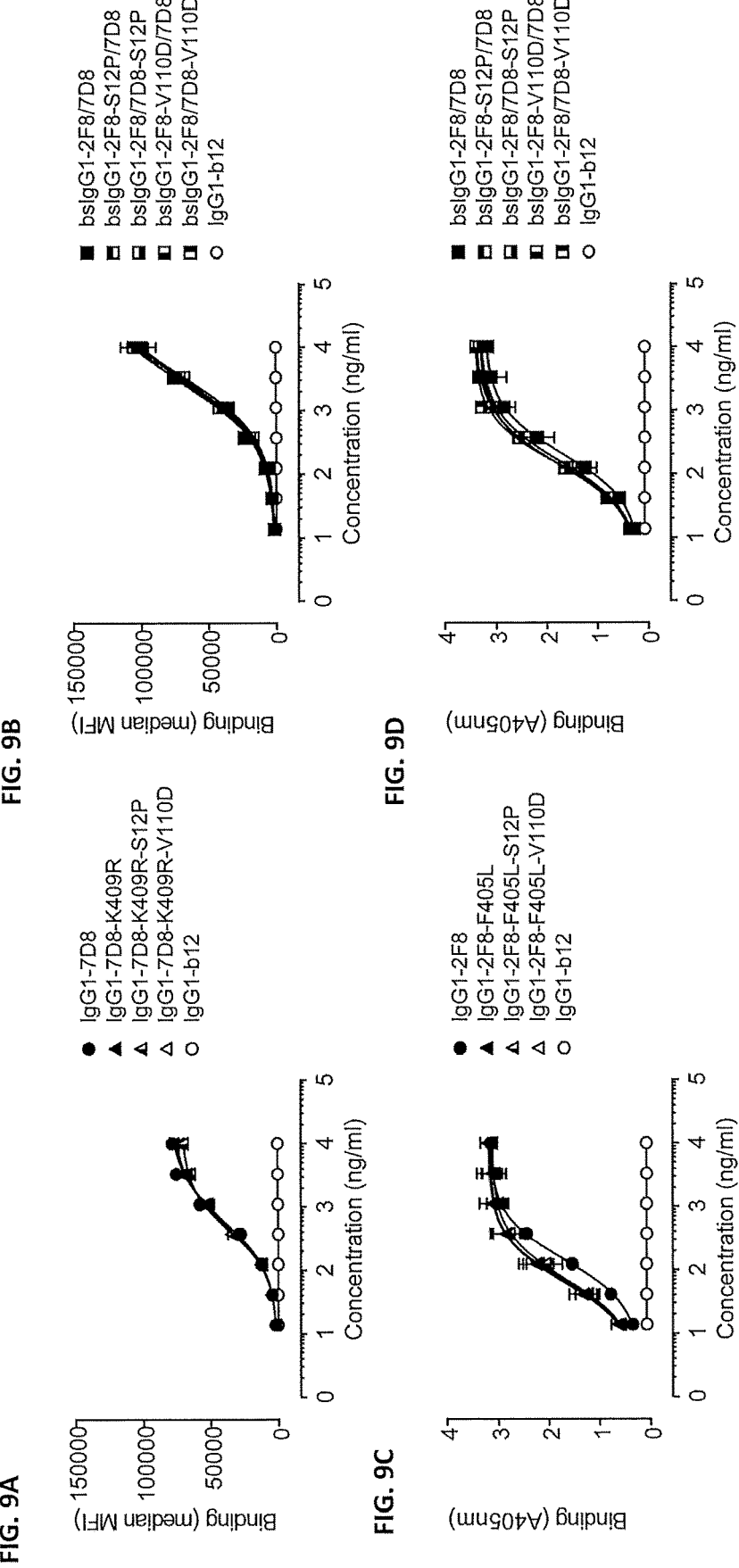

FIGS. 9A and 9B show that he binding of IgG-7D8 and bsIgG1-2F8×7D8 antibody variants to Ramos cells is comparable. FIGS. 9C and 9D show that he binding of IgG1-2F8 and bsIgG1-2F8×7D8 antibody variants to recombinant EGFR is comparable. Together, these data show that the S12P or V110D mutations do not affect antigen binding.

Example 20: CDC-Mediated Cell Kill of CD20-Expressing Cells by S12P or V110D Containing Antibodies The CD20 antibody IgG1-7D8 can efficiently kill CD20-expressing cells, such as Daudi cells, by complement-dependent cytotoxicity (CDC). It was previously shown that in the IgG1-7D8-K409R version of the antibody, the CDC activity was uncompromised (Labrijn et al., PNAS 2013, 110: 5145-50). Here, it was tested whether the mutants IgG1-7D8-K409R-S12P and IgG1-7D8-K409R-V110D were still able to induce CDC of CD20-expressing cells. The HIV-1 gp120-specific antibody IgG1-b12, not able to bind to Daudi cells was included as negative control.

$10^5$ Daudi cells were pre-incubated for 15 min with a concentration series of antibody in 80 µL RPMI medium supplemented with 0.1% BSA in a shaker at room temperature. 20 µL normal human serum (NHS) was added as a source of complement (20% NHS final concentration) and incubated for 45 min at 37° C. 30 µL ice cold RPMI medium supplemented with 0.1% BSA was added to stop the CDC reaction. Dead and viable cells were discriminated by adding 10 µL 10 µg/mL propidium iodide (PI) (1 µg/mL final concentration) and FACS analysis.

FIG. 10 shows the effect of the affinity knock-out mutations on antibody effector functions. FIG. 10A shows that CDC-mediated cell kill of CD20-expressing Daudi cells by IgG1-7D8, IgG1-7D8-K409R, IgG1-7D8-K409R-S12P and IgG1-7D8-K409R-V110D is comparable. The S12P or V110D mutations in the light chain therefore do not affect CDC. Daudi cells express CD20 but not EGFR, which results in monovalent binding of the bispecific antibodies-, bsIgG1-2F8/7D8, bsIgG1-2F8-S12P/7D8, bsIgG1-2F8/7D8-S12P, bsIgG1-2F8-V110D/7D8 and bsIgG1-2F8/7D8-V110D. FIG. 10B shows that all bispecific antibodies induce CDC-mediated cell kill of the CD20-expressing cells with comparable efficacy. These data indicate that the S12P or V110D mutations do not affect CDC.

Example 21: ADCC-Mediated Cell Kill of CD20-Expressing Cells by S12P or V110D Containing Antibodies Bispecific antibodies were generated by 2-MEA-induced controlled Fab-arm-exchange between IgG1-2F8-F405L× IgG1-7D8-K409R or IgG1-2F8-F405L-V110D×IgG1-7D8-K409R, bsIgG1-2F8/7D8 and bsIgG1-2F8-V110D/7D8, respectively.

The CD20 antibody IgG1-7D8 can also efficiently kill CD20-expressing cells, such as Daudi cells, by antibody-dependent cellular cytotoxicity (ADCC). It was previously shown that in the IgG1-7D8-K409R version of the antibody, the ADCC activity was uncompromised (Labrijn et al., PNAS 2013, 110: 5145-50). Here, it was tested whether the mutant mutant IgG1-7D8-S12P and IgG1-7D8-V110D were still able to induce ADCC of CD20-expressing cells. The HIV-1 gp120-specific antibody IgG1-b12, not able to bind to Daudi cells was included as negative control.

Peripheral blood mononuclear cells (PBMCs; effector cells) were isolated from whole blood of a healthy donor using Leucosep® tubes (Greiner Bio-one, cat. #227290) according to the manufacturer's recommendations. Target cells were labelled by adding 100 µCi $^{51}$Cr to 5×106 A431 cells in 1 mL RPMI medium supplemented with 0.1% BSA and incubating for 60 min in a 37° C. shaking water bath. Labelled cells were washed and resuspended in RPMI supplemented with 0.1% BSA. $5×10^4$ labelled target cells in RPMI supplemented with 0.1% BSA were preincubated in 100 µL for 15 min with the antibody concentrations series (range 0-10 µg/mL final concentration in ADCC assay in 3-fold dilutions) at room temperature. The ADCC assay was started by adding 50 µL effector cells ($5×10^6$ cells) in an E:T ratio 100:1. After 4 hours at 37° C., $^{51}$Cr release from triplicate experiments was measured in a scintillation counter as counts per min (cpm). The percentage of cellular toxicity was calculated using the following formula: percentage of specific lysis=(experimental cpm−basal cpm)/(maximal cpm−basal cpm)×100. Maximal $^{51}$Cr release was determined by adding 50 µL 5% Triton X-100 to 50 µL target cells ($5×10^4$ cells), and basal release was measured in the absence of sensitizing antibody and effector cells.

FIG. 10 shows the effect of the affinity knock-out mutations on antibody effector functions. FIG. 10C shows that ADCC-mediated cell kill of CD20-expressing Daudi cells by IgG1-7D8, IgG1-7D8-K409R, IgG1-7D8-K409R-S12P and IgG1-7D8-K409R-V110D is comparable. Daudi cells do not express EGFR, thus bsIgG1-2F8/7D8, bsIgG1-2F8-S12P/7D8, bsIgG1-2F8/7D8-S12P, bsIgG1-2F8-V110D/7D8 and bsIgG1-2F8/7D8-V110D bind monovalently. FIG. 10D shows that all bispecific antibodies induce ADCC-mediated cell kill of the CD20-expressing cells with comparable efficacy. Together, these data indicate that ADCC capacity is not affected by the V110D or S12P mutations.

Example 22: ADCC-Mediated Cell Kill of EGFR-Expressing Cells by V110D or S12P Containing Antibodies The EGFR antibody IgG1-2F8 can kill EGFR-expressing cells, such as A431, by ADCC. It was previously shown that in the IgG1-2F8-F405L version of the antibody, the ADCC activity was uncompromised (Labrijn et al., PNAS 2013, 110: 5145-50). Here, it was tested whether the mutants IgG1-2F8-F405L-V110D and IgG1-2F8-F405L-S12P were still able to induce ADCC of EGFR-expressing cells (as described in Example 21). A431 cells do not express CD20 or HIV-1 gp120 and therefore the CD20 antibody IgG1-7D8 and HIV-1 gp120 antibody IgG1-b12, do not induce ADCC of these cells.

FIG. 10 shows the effect of the affinity knock-out mutations on antibody effector functions. FIG. 10E shows that ADCC-mediated cell kill of EGFR-expressing A431 cells by IgG1-2F8-F405L, IgG1-2F8-F405L-V110D and IgG1-2F8-F405L-S12P is comparable. A431 cells do not express CD20, thus bsIgG1-2F8/7D8, bsIgG1-2F8-S12P/7D8, bsIgG1-2F8/7D8-S12P, bsIgG1-2F8-V110D/7D8 and bsIgG1-2F8/7D8-V110D bind monovalently. FIG. 10F shows that all bispecific antibodies induce ADCC-mediated cell kill of the EGFR-expressing cells with comparable efficacy. Together, these data indicate that ADCC capacity is not affected by the V110D or S12P mutations.

Example 23: In Vivo Analysis of the Pharmacokinetics of V110D Containing Antibodies The IgG1-2F8-F405L-V110D parental antibody and -bsIgG1-2F8/7D8 and bsIgG1-2F8-V110D/7D8, were injected into SCID mice to analyze their pharmacokinetic Total IgG concentrations in the plasma samples were assayed by ELISA. In short, ELISA plates (Greiner bio-one, Frickenhausen, Germany) were coated overnight with 2 µg/mL (100 µL/well) mouse anti-human IgG (clone MH16-1; CLB; cat. no. M1268) in PBS at 4° C. The plates were washed once with PBST. Dilution series of serum samples in PBST/0.2% BSA (PBSTB) were transferred to the coated ELISA plates (100 µL/well) and incubated on a plate shaker (300 rpm) for 60 min at room temperature (RT). Samples were discarded and the plates were washed once with PBS/0.05% Tween 20 (PBST). Next, the plates were incubated on a plate shaker (300 rpm) with HRP-conjugated goat anti-human IgG (clone 11H; Jackson; cat. no. 109-035-098; 1:10,000) in PBSTB (100 µL/well) for 60 min at RT. The plates were washed once with PBS/0.05% Tween 20 (PBST). ABTS (50 mg/mL; Roche Diagnostics GmbH®, Mannheim, Germany) was added (100 µL/well) and incubated protected from light for 30 min at RT. The reaction was stopped with 2% oxalic acid (100 µL/well; Riedel de Haen, Seelze, Germany). After 10 min at RT, absorbance at 405 nm was measured in an ELISA plate reader.

FIG. 11A and FIG. 11B show total antibody plasma concentrations and plasma clearance rates, respectively. The pharmacokinetic profiles and clearance rates were identical in all groups, and similar to historical data of WT IgG1 (the predicted levels in FIG. 11A). This indicates that the pharmacokinetic properties are not affected by the V110D mutation.

TABLE 1

| IgG1-2F8-F405L and IgG1-7D8-K409R Kappa L-chain variants | | |
|---|---|---|
| IgG1-2F8-F405L-mmCL(F135L) | IgG1-2F8-F405L-G157N | IgG1-2F8-F405L-S182T |
| IgG1-2F8-F405L-V110D | IgG1-2F8-F405L-N158G | IgG1-2F8-F405L-A193T |
| IgG1-2F8-F405L-E143D | IgG1-2F8-F405L-E161N | IgG1-2F8-F405L-T206V |
| IgG1-2F8-F405L-A144I | IgG1-2F8-F405L-E165D | |
| IgG1-2F8-F405L-S9L | IgG1-2F8-F405L-S12P | IgG1-2F8-F405L-R18P |
| IgG1-2F8-F405L-T20S-T22S | IgG1-2F8-F405L-R24S | IgG1-2F8-F405L-K107L |
| IgG1-7D8-K409R-V110A | IgG1-7D8-K409R-V110D | IgG1-7D8-K409R-V110E |
| IgG1-7D8-K409R-V110F | IgG1-7D8-K409R-V110G | IgG1-7D8-K409R-V110H |
| IgG1-7D8-K409R-V110I | IgG1-7D8-K409R-V110K | IgG1-7D8-K409R-V110L |
| IgG1-7D8-K409R-V110M | IgG1-7D8-K409R-V110N | IgG1-7D8-K409R-V110P |
| IgG1-7D8-K409R-V110Q | IgG1-7D8-K409R-V110R | IgG1-7D8-K409R-V110S |
| IgG1-7D8-K409R-V110T | IgG1-7D8-K409R-V110W | IgG1-7D8-K409R-V110Y | properties. For this three groups of mice (3 mice per group) were injected intravenously in the tail vein with 200 µL purified antibody: (1) 100 µg(/mouse) bsIgG1-2F8/7D8; (2) 100 µg bsIgG1-2F8-V110D/7D8; (3) 100 µg IgG1-2F8-F405L-V110D. Blood samples (50-100 µL) were collected by cheek puncture at pre-determined time intervals after antibody administration (10 min, 3 h, 1, 2, 7, 14, 21 days). Blood was collected into heparin containing vials and centrifuged for 10 min at 14,000 g. Plasma was stored at −20° C. before further analysis.

In a separate experiment, the IgG1-2F8-F405L-S12P parental antibody and bsIgG1-2F8/7D8 and bsIgG1-2F8-S12P/7D8, were injected into SCID mice to analyze their pharmacokinetic properties. Like described above, groups (3 mice per group) were injected intravenously in the tail vein with: (1) 100 µg(/mouse) bsIgG1-2F8/7D8; (2) 100 µg bsIgG1-2F8-S12P/7D8; or (3) 100 µg IgG1-2F8-F405L-S12P. Blood samples (50-100 µL) were collected by cheek puncture at pre-determined time intervals after antibody administration (10 min, 3 h, 1, 2, 7, 15, 21 days). Blood was collected into heparin containing vials and centrifuged for 10 min at 14,000 g. Plasma was stored at −20° C. before further analysis.

TABLE 2

Binding behavior IgG1-2F8-F405L and Variants to KappaSelect resin

| IgG1-2F8-F405L variant | Affinity |
|---|---|
| IgG1-2F8-F405L | +++ |
| IgG1-2F8-F405L-V110D | − |
| IgG1-2F8-F405L-E143D | ++ |
| IgG1-2F8-F405L-A144I | +++ |
| IgG1-2F8-F405L-G157N | +++ |
| IgG1-2F8-F405L-N158G | +++ |
| IgG1-2F8-F405L-E161N | +++ |
| IgG1-2F8-F405L-E165D | +++ |
| IgG1-2F8-F405L-S182T | +++ |

TABLE 3

| Binding behavior IgG1-7D8-K409R and Variants to CaptureSelect KappaXL resin | |
|---|---|
| IgG1-7D8-K409R variant | Affinity |
| IgG1-7D8-K409R | +++ |
| IgG1-7D8-K409R-V110A | +++ |
| IgG1-7D8-K409R-V110D | – |
| IgG1-7D8-K409R-V110E | + |
| IgG1-7D8-K409R-V110F | ++ |
| IgG1-7D8-K409R-V110G | +++ |
| IgG1-7D8-K409R-V110H | + |
| IgG1-7D8-K409R-V110I | ++ |
| IgG1-7D8-K409R-V110K | + |
| IgG1-7D8-K409R-V110L | +++ |
| IgG1-7D8-K409R-V110M | +++ |
| IgG1-7D8-K409R-V110N | + |
| IgG1-7D8-K409R-V110P | + |
| IgG1-7D8-K409R-V110Q | + |
| IgG1-7D8-K409R-V110R | – |
| IgG1-7D8-K409R-V110S | ++ |
| IgG1-7D8-K409R-V110T | ++ |
| IgG1-7D8-K409R-V110W | + |
| IgG1-7D8-K409R-V110Y | ++ |

TABLE 4

| Binding behavior IgG1-2F8-F405L and Variants to Protein L resin | |
|---|---|
| IgG1-2F8-F405L variant | Affinity |
| IgG1-2F8-F405L | +++ |
| IgG1-2F8-F405L-S9L | +++ |
| IgG1-2F8-F405L-S12P | – |
| IgG1-2F8-F405L-R18P | +++ |
| IgG1-2F8-F405L-T20S-T22S | +++ |
| IgG1-2F8-F405L-R24S | +++ |
| IgG1-2F8-F405L-K107L | +++ |

TABLE 5

| Melting point determination of IgG1 variants determined by differential scanning fluorimetry | | |
|---|---|---|
| Antibody variant | Average Tm1 (° C.) | Average Tm2 (° C.) |
| IgG1-2F8-F405L | 67.0 | 74.5 |
| IgG1-2F8-F405L-S12P | 67.0 | 74.5 |
| IgG1-2F8-F405L-V110D | 67.0 | 74.5 |
| IgG1-7D8-K409R | 66.3 | — |
| BsIgG1-2F8/7D8 | 67.5 | 73.5 |
| BsIG1-2F8-S12P/7D8 | 67.3 | 73.5 |
| BsG1-2F8-V110D/7D8 | 67.5 | 73.5 |

The invention claimed is:

1. A bispecific or multispecific antibody comprising:
   (a) a first light chain/heavy chain pair comprising a first VL region and a first VH region having a first binding specificity and comprising a first kappa light chain constant region and a first heavy chain constant region; and
   (b) a second light chain/heavy chain pair comprising a second VL region and a second VH region having a second binding specificity and comprising a second kappa light chain constant region and a second heavy chain constant region;
   wherein the first kappa light chain constant region comprises the amino acid substitution V110D or E143D, or both amino acid substitutions V110D and E143D, according to the EU numbering system.

2. The bispecific or multispecific antibody of claim 1, wherein the first kappa light chain constant region comprises the amino acid substitution V110D, according to the EU numbering system.

3. The bispecific or multispecific antibody of claim 1, wherein the first kappa light chain constant region comprises the amino acid substitution E143D, according to the EU numbering system.

4. The bispecific or multispecific antibody of claim 1, wherein the second kappa light chain constant region comprises the amino acid substitution V110D or E143D, or both amino acid substitutions V110D and E143D, according to the EU numbering system.

5. The bispecific or multispecific antibody of claim 1, wherein the second kappa light chain constant region comprises the amino acid substitution V110D, according to the EU numbering system.

6. The bispecific or multispecific antibody of claim 1, wherein the second kappa light chain constant region comprises the amino acid substitution E143D, according to the EU numbering system.

7. The bispecific or multispecific antibody of claim 4, wherein the first and second kappa light chain constant regions do not contain amino acid substitutions in the same positions.

8. The bispecific or multispecific antibody of claim 1, which is a bispecific antibody.

9. The bispecific or multispecific antibody of claim 1, which is a multispecific antibody.

10. The bispecific or multispecific antibody of claim 1, wherein the first kappa light chain constant region comprises both amino acid substitutions V110D and E143D.

11. The bispecific or multispecific antibody of claim 1, wherein the second kappa light chain constant region comprises both amino acid substitutions V110D and E143D.

12. The bispecific or multispecific antibody of claim 1, wherein the bispecific or multispecific antibody has reduced affinity for an affinity reagent compared to the bispecific or multispecific antibody without the amino acid substitution in said first kappa light chain constant region.

13. The bispecific or multispecific antibody of claim 2, which is a bispecific antibody.

14. The bispecific or multispecific antibody of claim 4, which is a bispecific antibody.

15. The bispecific or multispecific antibody of claim 1, wherein said first and second kappa light chains are human kappa light chains.

16. A bispecific or multispecific antibody comprising:
   (a) a first light chain/heavy chain pair comprising a first VL region and a first VH region having a first binding specificity and comprising a first kappa light chain constant region and a first heavy chain constant region; and
   (b) a second light chain/heavy chain pair comprising a second VL region and a second VH region having a second binding specificity and comprising a second kappa light chain constant region and a second heavy chain constant region;
   wherein the first kappa light chain constant region comprises an amino acid substitution at a position corresponding to position V110 or position E143, according to the EU numbering system, wherein the amino acid substitution is selected from the group consisting of V110D, V110R, V110E, V110H, V110K, V110N, V110P, V110Q, V110W, and E143D, wherein the second kappa light chain does not comprise an amino acid substitution at a position corresponding to position V110 or position E143, according to the EU numbering system, and wherein the first and second kappa light chain constant regions do not contain amino acid substitutions in the same positions.

17. The bispecific or multispecific antibody of claim 16, wherein the first kappa light chain constant region comprises the amino acid substitution V110D, according to the EU numbering system.

18. The bispecific or multispecific antibody of claim 16, wherein the first kappa light chain constant region comprises the amino acid substitution E143D, according to the EU numbering system.

19. The bispecific or multispecific antibody of claim 16, wherein the first kappa light chain constant region comprises the amino acid substitutions V110D and E143D, according to the EU numbering system.

20. The bispecific or multispecific antibody of claim 16, which is a bispecific antibody.

21. The bispecific or multispecific antibody of claim 16, which is a multispecific antibody.

22. The bispecific or multispecific antibody of claim 16, wherein said first and second kappa light chains are human kappa light chains.

* * * * *

SEQUENCE LISTING

<160> NUMBER OF SEQ ID NOS: 27

<210> SEQ ID NO 1
<211> LENGTH: 106
<212> TYPE: PRT
<213> ORGANISM: Homo sapiens

<400> SEQUENCE: 1

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 2
<211> LENGTH: 106
<212> TYPE: PRT
<213> ORGANISM: Homo sapiens

<400> SEQUENCE: 2

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30
```

```
Pro Arg Glu Ala Lys Val Gln Trp Lys Val Asp Asn Ala Leu Gln Ser
        35              40              45

Gly Asn Ser Gln Glu Ser Val Thr Glu Gln Glu Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Gly Glu Val Thr His Gln Gly Leu Ser Ser Pro
                85              90              95

Val Thr Lys Ser Phe Asn Arg Gly Glu Cys
            100             105

<210> SEQ ID NO 3
<211> LENGTH: 106
<212> TYPE: PRT
<213> ORGANISM: Homo sapiens

<400> SEQUENCE: 3

Thr Val Ala Ala Pro Ser Val Phe Ile Phe Pro Pro Ser Asp Glu Gln
1               5               10              15

Leu Lys Ser Gly Thr Ala Ser Val Val Cys Leu Leu Asn Asn Phe Tyr
            20              25              30

Pro Arg Glu Ala Lys Val Gln Arg Lys Val Asp Asn Ala Leu Gln Ser
        35              40              45

Gly Asn Ser Gln Glu Ser Val Thr Glu Gln Glu Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Cys Glu Val Thr His Gln Gly Leu Ser Ser Pro
                85              90              95

Val Thr Lys Ser Phe Asn Arg Gly Glu Cys
            100             105

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5               10              15

Leu Lys Ser Gly Thr Ala Ser Val Val Cys Leu Leu Asn Asn Phe Tyr
            20              25              30

Pro Arg Glu Ala Lys Val Gln Trp Lys Val Asp Asn Val Leu Gln Ser
        35              40              45

Gly Asn Ser Gln Glu Ser Val Thr Glu Gln Asp Ser Lys Asp Ser Thr
    50              55              60

Tyr Ser Leu Ser Ser Thr Leu Thr Leu Ser Lys Ala Asp Tyr Glu Lys
65              70              75              80

His Lys Leu Tyr Ala Cys Glu Val Thr His Gln Gly Leu Ser Ser Pro
                85              90              95

Val Thr Lys Ser Phe Asn Arg Gly Glu Cys
            100             105

<210> SEQ ID NO 5
<211> LENGTH: 106
<212> TYPE: PRT
<213> ORGANISM: Homo sapiens
```

<400> SEQUENCE: 5

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Asn Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 6
<211> LENGTH: 106
<212> TYPE: PRT
<213> ORGANISM: Macaca fascicularis

<400> SEQUENCE: 6

Ala Val Ala Ala Pro Ser Val Phe Ile Phe Pro Pro Ser Glu Asp Gln
1               5                   10                  15

Val Lys Ser Gly Thr Val Ser Val Val Cys Leu Leu Asn Asn Phe Tyr
            20                  25                  30

Pro Arg Glu Ala Ser Val Lys Trp Lys Val Asp Gly Ala Val Gln Thr
        35                  40                  45

Gly Asn Ser Gln Glu Ser Val Thr Glu Gln Asp Ser Lys Asp Asn Thr
    50                  55                  60

Tyr Ser Leu Ser Ser Thr Leu Thr Leu Ser Ser Thr Asp Tyr Gln Ser
65                  70                  75                  80

His Asn Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 7
<211> LENGTH: 106
<212> TYPE: PRT
<213> ORGANISM: Macaca mulatta

<400> SEQUENCE: 7

Ala Val Ala Ala Pro Ser Val Leu Ile Phe Pro Pro Ser Glu Asp Gln
1               5                   10                  15

Val Lys Ser Gly Thr Val Ser Val Val Cys Leu Leu Asn Asn Phe Tyr
            20                  25                  30

Pro Arg Glu Ala Ser Val Lys Trp Lys Val Asp Gly Val Leu Lys Thr
        35                  40                  45

Gly Asn Ser Gln Glu Ser Val Thr Glu Gln Asp Ser Lys Asp Asn Thr
    50                  55                  60

Tyr Ser Leu Ser Ser Thr Leu Thr Leu Ser Ser Thr Asp Tyr Gln Ser
65                  70                  75                  80

His Asn Val Tyr Ala Cys Glu Val Thr His Gln Gly Leu Ser Ser Pro
                85                  90                  95

Val Thr Lys Ser Phe Asn Arg Gly Glu Cys

-continued

```
                100                 105

<210> SEQ ID NO 8
<211> LENGTH: 106
<212> TYPE: PRT
<213> ORGANISM: Mus musculus

<400> SEQUENCE: 8

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 9
<211> LENGTH: 103
<212> TYPE: PRT
<213> ORGANISM: Mus musculus

<400> SEQUENCE: 9

Pro Lys Ser Thr Pro Thr Leu Thr Val Phe Pro Pro Ser Ser Glu Glu
1               5                   10                  15

Leu Lys Glu Asn Lys Ala Thr Leu Val Cys Leu Ile Ser Asn Phe Ser
            20                  25                  30

Pro Ser Gly Val Thr Val Ala Trp Lys Ala Asn Gly Thr Pro Ile Thr
        35                  40                  45

Gln Gly Val Asp Thr Ser Asn Pro Thr Lys Glu Gly Asn Lys Phe Met
    50                  55                  60

Ala Ser Ser Phe Leu His Leu Thr Ser Asp Gln Trp Arg Ser His Asn
65                  70                  75                  80

Ser Phe Thr Cys Gln Val Thr His Glu Gly Asp Thr Val Glu Lys Ser
                85                  90                  95

Leu Ser Pro Ala Glu Cys Leu
            100

<210> SEQ ID NO 10
<211> LENGTH: 103
<212> TYPE: PRT
<213> ORGANISM: Mus musculus

<400> SEQUENCE: 10

Pro Lys Ser Thr Pro Thr Leu Thr Met Phe Pro Pro Ser Pro Glu Glu
1               5                   10                  15

Leu Gln Glu Asn Lys Ala Thr Leu Val Cys Leu Ile Ser Asn Phe Ser
            20                  25                  30

Pro Ser Gly Val Thr Val Ala Trp Lys Ala Asn Gly Thr Pro Ile Thr
        35                  40                  45

Gln Gly Val Asp Thr Ser Asn Pro Thr Lys Glu Asp Asn Lys Tyr Met
    50                  55                  60
```

Ala Ser Ser Phe Leu His Leu Thr Ser Asp Gln Trp Arg Ser His Asn
65                  70                  75                  80

Ser Phe Thr Cys Gln Val Thr His Glu Gly Asp Thr Val Glu Lys Ser
                85                  90                  95

Leu Ser Pro Ala Glu Cys Leu
            100

<210> SEQ ID NO 11
<211> LENGTH: 104
<212> TYPE: PRT
<213> ORGANISM: Homo sapiens

<400> SEQUENCE: 11

Pro Lys Ala Asn Pro Thr Val Thr Leu Phe Pro Pro Ser Ser Glu Glu
1                   5                   10                  15

Leu Gln Ala Asn Lys Ala Thr Leu Val Cys Leu Ile Ser Asp Phe Tyr
                20                  25                  30

Pro Gly Ala Val Thr Val Ala Trp Lys Ala Asp Gly Ser Pro Val Lys
            35                  40                  45

Ala Gly Val Glu Thr Thr Lys Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 12
<211> LENGTH: 104
<212> TYPE: PRT
<213> ORGANISM: Homo sapiens

<400> SEQUENCE: 12

Pro Lys Ala Ala Pro Ser Val Thr Leu Phe Pro Pro Ser Ser Glu Glu
1                   5                   10                  15

Leu Gln Ala Asn Lys Ala Thr Leu Val Cys Leu Ile Ser Asp Phe Tyr
                20                  25                  30

Pro Gly Ala Val Thr Val Ala Trp Lys Ala Asp Ser Ser Pro Val Lys
            35                  40                  45

Ala Gly Val Glu Thr Thr Thr Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 13
<211> LENGTH: 104
<212> TYPE: PRT
<213> ORGANISM: Homo sapiens

<400> SEQUENCE: 13

Pro Lys Ala Ala Pro Ser Val Thr Leu Phe Pro Pro Ser Ser Glu Glu
1                   5                   10                  15

```
Leu Gln Ala Asn Lys Ala Thr Leu Val Cys Leu Ile Ser Asp Phe Tyr
        20                  25                  30

Pro Gly Ala Val Thr Val Ala Trp Lys Ala Asp Ser Ser Pro Ala Lys
        35                  40                  45

Ala Gly Val Glu Thr Thr Thr Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                    85                  90                  95

Thr Val Ala Pro Thr Glu Cys Ser
            100

<210> SEQ ID NO 14
<211> LENGTH: 104
<212> TYPE: PRT
<213> ORGANISM: Homo sapiens

<400> SEQUENCE: 14

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
        20                  25                  30

Pro Gly Ala Val Lys Val Ala Trp Lys Ala Asp Gly Ser Pro Val Asn
        35                  40                  45

Thr Gly Val Glu Thr Thr Thr Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                    85                  90                  95

Thr Val Ala Pro Ala Glu Cys Ser
            100

<210> SEQ ID NO 15
<211> LENGTH: 104
<212> TYPE: PRT
<213> ORGANISM: Homo sapiens

<400> SEQUENCE: 15

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Val Ser Asp Phe Tyr
        20                  25                  30

Pro Gly Ala Val Thr Val Ala Trp Lys Ala Asp Gly Ser Pro Val Lys
        35                  40                  45

Val Gly Val Glu Thr Thr Lys Pro Ser Lys Gln Ser Asn Asn Lys Tyr
        50                  55                  60

Ala Ala Ser Ser Tyr Leu Ser Leu Thr Pro Glu Gln Trp Lys Ser His
65                  70                  75                  80

Arg Ser Tyr Ser Cys Arg Val Thr His Glu Gly Ser Thr Val Glu Lys
                    85                  90                  95

Thr Val Ala Pro Ala Glu Cys Ser
            100

<210> SEQ ID NO 16
<211> LENGTH: 106
```

<212> TYPE: PRT
<213> ORGANISM: Rattus norvegicus

<400> SEQUENCE: 16

Ala Asp Ala Ala Pro Thr Val Ser Ile Phe Pro Pro Ser Thr Glu Gln
1               5                   10                  15

Leu Ala Thr Gly Gly Ala Ser Val Val Cys Leu Met Asn Asn Phe Tyr
            20                  25                  30

Pro Arg Asp Ile Ser Val Lys Trp Lys Ile Asp Gly Thr Glu Arg Arg
        35                  40                  45

Asp Gly Val Leu Asp Ser Val Thr Asp Gln Asp Ser Lys Asp Ser Thr
    50                  55                  60

Tyr Ser Met Ser Ser Thr Leu Ser Leu Thr Lys Ala Asp Tyr Glu Ser
65                  70                  75                  80

His Asn Leu Tyr Thr Cys Glu Val Val His Lys Thr Ser Ser Ser Pro
                85                  90                  95

Val Val Lys Ser Phe Asn Arg Asn Glu Cys
            100                 105

<210> SEQ ID NO 17
<211> LENGTH: 103
<212> TYPE: PRT
<213> ORGANISM: Oryctolagus cuniculus

<400> SEQUENCE: 17

Asp Pro Val Ala Pro Thr Val Leu Ile Phe Pro Pro Ala Ala Asp Gln
1               5                   10                  15

Val Ala Thr Gly Thr Val Thr Ile Val Cys Val Ala Asn Lys Tyr Phe
            20                  25                  30

Pro Asp Val Thr Val Thr Trp Glu Val Asp Gly Thr Thr Gln Thr Thr
        35                  40                  45

Gly Ile Glu Asn Ser Lys Thr Pro Gln Asn Ser Ala Asp Cys Thr Tyr
    50                  55                  60

Asn Leu Ser Ser Thr Leu Thr Leu Thr Ser Thr Gln Tyr Asn Ser His
65                  70                  75                  80

Lys Glu Tyr Thr Cys Lys Val Thr Gln Gly Thr Thr Ser Val Val Gln
                85                  90                  95

Ser Phe Asn Arg Gly Asp Cys
            100

<210> SEQ ID NO 18
<211> LENGTH: 105
<212> TYPE: PRT
<213> ORGANISM: Oryctolagus cuniculus

<400> SEQUENCE: 18

Asp Pro Val Ala Pro Ser Val Leu Leu Phe Pro Pro Ser Lys Glu Glu
1               5                   10                  15

Leu Thr Thr Gly Thr Ala Thr Ile Val Cys Val Ala Asn Lys Phe Tyr
            20                  25                  30

Pro Ser Asp Ile Thr Val Thr Trp Lys Val Asp Gly Thr Thr Gln Gln
        35                  40                  45

Ser Gly Ile Glu Asn Ser Lys Thr Pro Gln Ser Pro Glu Asp Asn Thr
    50                  55                  60

Tyr Ser Leu Ser Ser Thr Leu Ser Leu Thr Ser Ala Gln Tyr Asn Ser
65                  70                  75                  80

His Ser Val Tyr Thr Cys Glu Val Val Gln Gly Ser Ala Ser Pro Ile

```
                    85                  90                  95

Val Gln Ser Phe Asn Arg Gly Asp Cys
                   100                 105

<210> SEQ ID NO 19
<211> LENGTH: 107
<212> TYPE: PRT
<213> ORGANISM: Bos taurus

<400> SEQUENCE: 19

Ser Asp Ala Glu Pro Ser Val Phe Leu Phe Lys Pro Ser Asp Glu Gln
1               5                   10                  15

Leu Lys Thr Gly Thr Val Ser Val Val Cys Leu Val Asn Asp Phe Tyr
               20                  25                  30

Pro Lys Asp Ile Asn Val Lys Trp Lys Val Asp Gly Val Thr Gln Ser
           35                  40                  45

Ser Ser Asn Phe Gln Asn Ser Phe Thr Asp Gln Asp Ser Lys Lys Ser
       50                  55                  60

Thr Tyr Ser Leu Ser Ser Ile Leu Thr Leu Pro Ser Ser Glu Tyr Gln
65                  70                  75                  80

Ser His Asn Ala Tyr Thr Cys Glu Val Ser His Lys Ser Leu Thr Thr
                   85                  90                  95

Ala Leu Val Lys Ser Phe Ser Lys Asn Glu Cys
               100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(1)
<223> OTHER INFORMATION: X is A or T
<220> FEATURE:
<221> NAME/KEY: misc_feature
<222> LOCATION: (8)..(8)
<223> OTHER INFORMATION: X is F OR L
<220> FEATURE:
<221> NAME/KEY: misc_feature
<222> LOCATION: (14)..(14)
<223> OTHER INFORMATION: X is D or E
<220> FEATURE:
<221> NAME/KEY: misc_feature
<222> LOCATION: (15)..(15)
<223> OTHER INFORMATION: X is E or D
<220> FEATURE:
<221> NAME/KEY: misc_feature
<222> LOCATION: (17)..(17)
<223> OTHER INFORMATION: X is L or V
<220> FEATURE:
<221> NAME/KEY: misc_feature
<222> LOCATION: (22)..(22)
<223> OTHER INFORMATION: X is A or V
<220> FEATURE:
<221> NAME/KEY: misc_feature
<222> LOCATION: (37)..(37)
<223> OTHER INFORMATION: X is K or S
<220> FEATURE:
<221> NAME/KEY: misc_feature
<222> LOCATION: (39)..(39)
<223> OTHER INFORMATION: X is Q or K
<220> FEATURE:
<221> NAME/KEY: misc_feature
<222> LOCATION: (40)..(40)
<223> OTHER INFORMATION: X is W or R
<220> FEATURE:
<221> NAME/KEY: misc_feature
```

```
<222> LOCATION: (44)..(44)
<223> OTHER INFORMATION: X is N or G
<220> FEATURE:
<221> NAME/KEY: misc_feature
<222> LOCATION: (45)..(45)
<223> OTHER INFORMATION: X is A or V
<220> FEATURE:
<221> NAME/KEY: misc_feature
<222> LOCATION: (46)..(46)
<223> OTHER INFORMATION: X is L or V
<220> FEATURE:
<221> NAME/KEY: misc_feature
<222> LOCATION: (47)..(47)
<223> OTHER INFORMATION: X is Q or K
<220> FEATURE:
<221> NAME/KEY: misc_feature
<222> LOCATION: (48)..(48)
<223> OTHER INFORMATION: X is S or T
<220> FEATURE:
<221> NAME/KEY: misc_feature
<222> LOCATION: (59)..(59)
<223> OTHER INFORMATION: X is D or E
<220> FEATURE:
<221> NAME/KEY: misc_feature
<222> LOCATION: (63)..(63)
<223> OTHER INFORMATION: X is S or N
<220> FEATURE:
<221> NAME/KEY: misc_feature
<222> LOCATION: (69)..(69)
<223> OTHER INFORMATION: X is S or N
<220> FEATURE:
<221> NAME/KEY: misc_feature
<222> LOCATION: (75)..(75)
<223> OTHER INFORMATION: X is K or S
<220> FEATURE:
<221> NAME/KEY: misc_feature
<222> LOCATION: (76)..(76)
<223> OTHER INFORMATION: X is A or T
<220> FEATURE:
<221> NAME/KEY: misc_feature
<222> LOCATION: (79)..(79)
<223> OTHER INFORMATION: X is E or Q
<220> FEATURE:
<221> NAME/KEY: misc_feature
<222> LOCATION: (80)..(80)
<223> OTHER INFORMATION: X is K or S
<220> FEATURE:
<221> NAME/KEY: misc_feature
<222> LOCATION: (82)..(82)
<223> OTHER INFORMATION: X is K or N
<220> FEATURE:
<221> NAME/KEY: misc_feature
<222> LOCATION: (83)..(83)
<223> OTHER INFORMATION: X is V or L
<220> FEATURE:
<221> NAME/KEY: misc_feature
<222> LOCATION: (86)..(86)
<223> OTHER INFORMATION: X is C or G

<400> SEQUENCE: 20

Xaa Val Ala Ala Pro Ser Val Xaa Ile Phe Pro Pro Ser Xaa Xaa Gln
1               5                   10                  15

Xaa Lys Ser Gly Thr Xaa Ser Val Val Cys Leu Leu Asn Asn Phe Tyr
            20                  25                  30

Pro Arg Glu Ala Xaa Val Xaa Xaa Lys Val Asp Xaa Xaa Xaa Xaa Xaa
            35                  40                  45

Gly Asn Ser Gln Glu Ser Val Thr Glu Gln Xaa Ser Lys Asp Xaa Thr
        50                  55                  60

Tyr Ser Leu Ser Xaa Thr Leu Thr Leu Ser Xaa Xaa Asp Tyr Xaa Xaa
65                  70                  75                  80

His Xaa Xaa Tyr Ala Xaa Glu Val Thr His Gln Gly Leu Ser Ser Pro
                85                  90                  95
```

```
Val Thr Lys Ser Phe Asn Arg Gly Glu Cys
            100                 105

<210> SEQ ID NO 21
<211> LENGTH: 113
<212> TYPE: PRT
<213> ORGANISM: Homo sapiens

<400> SEQUENCE: 21

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Arg Gly Ser Gly Thr Asp Phe Thr Leu Thr
65                  70                  75                  80

Ile Ser Ser Val Gln Ala Glu Asp Gln Ala Val Tyr Tyr Cys Lys Gln
                85                  90                  95

Ala Tyr Ile Pro Pro Leu Thr Phe Gly Ala Gly Thr Lys Leu Glu Leu
            100                 105                 110

Lys

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Homo sapiens

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45
```

```
Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 24
<211> LENGTH: 112
<212> TYPE: PRT
<213> ORGANISM: Homo sapiens

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Phe Asp Tyr Leu Asn Trp Tyr Leu Gln Lys Pro Gly Gln Ser
            35                  40                  45

Pro Glx Leu Leu Ile Tyr Ala Leu Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Glx Ala
                85                  90                  95

Leu Gln Ala Pro Ile Thr Phe Gly Gln Gly Thr Arg Leu Glu Ile Lys
            100                 105                 110

<210> SEQ ID NO 25
<211> LENGTH: 110
<212> TYPE: PRT
<213> ORGANISM: Homo sapiens

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Gly Asn Phe Asp Ile Gly Arg Asn
                20                  25                  30

Ser Val Asn Trp Tyr Gln Val His Pro Gly Thr Ala Pro Arg Leu Leu
            35                  40                  45

Ile Tyr Ser Ser Asp Gln Arg Ser Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asn Glu Ala Asp Tyr Phe Cys Ala Thr Trp Asp Asp Ser Leu
                85                  90                  95

Asp Gly Pro Val Phe Gly Gly Gly Thr Lys Val Thr Val Leu
            100                 105                 110

<210> SEQ ID NO 26
<211> LENGTH: 330
<212> TYPE: PRT
<213> ORGANISM: Homo sapiens

<400> SEQUENCE: 26
```

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 107
<212> TYPE: PRT
<213> ORGANISM: Homo sapiens

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
        35                  40                  45
```

-continued

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```